United States Patent [19]

Astles et al.

[11] Patent Number: 5,139,563

[45] Date of Patent: Aug. 18, 1992

[54] HERBICIDAL COMPOUNDS

[75] Inventors: David P. Astles, Sittingbourne; Andrew Flood, Cowley, both of England; Alastair McArthur, Rotterdam/Pernis, Netherlands; Trevor W. Newton, Sittingbourne, England; John E. Spencer, Liverpool, England; David C. Hunter, Sittingbourne, England

[73] Assignee: Shell Research Limited, United Kingdom

[21] Appl. No.: 529,368

[22] Filed: May 30, 1990

[30] Foreign Application Priority Data

Jun. 2, 1989 [GB] United Kingdom ............... 8912700

[51] Int. Cl.$^5$ .................. C07D 239/34; C07D 239/52; C07D 403/12; A01N 43/54

[52] U.S. Cl. .......................................... 71/92; 71/90; 544/296; 544/299; 544/300; 544/301; 544/302; 544/303; 544/304; 544/309; 544/310; 544/312; 544/313; 544/314; 544/315; 544/316; 544/317; 544/318

[58] Field of Search ...................... 71/92, 90; 544/318, 544/296, 299, 302, 309, 313, 316

[56] References Cited

U.S. PATENT DOCUMENTS

| | | | |
|---|---|---|---|
| 3,920,648 | 11/1975 | Hardtmann | 544/318 |
| 4,871,387 | 10/1989 | Sasse et al. | 71/92 |
| 4,889,552 | 12/1989 | Wada et al. | 71/92 |

FOREIGN PATENT DOCUMENTS

| | | |
|---|---|---|
| 30138 | 6/1981 | European Pat. Off. . |
| 347811 | 12/1989 | European Pat. Off. . |
| 109170 | 10/1974 | German Democratic Rep. . |
| 814947 | 6/1959 | United Kingdom . |
| 1132306 | 10/1968 | United Kingdom . |

OTHER PUBLICATIONS

Gefenas et al., Chemical Abstracts, vol. 102, entry 62185x (1985).
Gomarasca et al., Chemical Abstracts, vol. 100, entry 6538m (1984).
H. Koopman, Rec. Trav. Chim., vol. 78, pp. 967–980 (1959).
H. Koopman, Rec. Trav. Chim., vol. 79, pp. 83–89 (1960).

Primary Examiner—John M. Ford

[57] ABSTRACT

Compounds of formula I

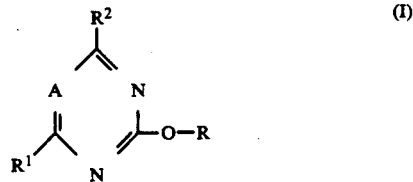

wherein
A is nitrogen or a group $CR^5$;
each of $R^1$, $R^2$ and $R^5$ is, independently, hydrogen, halogen, formyl, cyano, carboxy, azido or optionally substituted alkyl, alkenyl, alkynyl, cycloalkyl, alkoxy, alkenyloxy, alkynyloxy, aryloxy, alkylthio, alkenylthio, alkynylthio, arylthio, alkylcarbonyl, alkoxycarbonyl, amino, aminoxy or dialkyliminoxy; and
R is

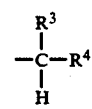

in which $R^3$ is hydrogen, optionally substituted alkyl, alkenyl, alkynyl, cycloalkyl, heterocyclic or aryl, or $COR^8$, $R^8$ being hydroxy, alkoxy, carboxy, alkoxycarbonyl, amino or mono- or di- alkylamino; and
$R^4$ is a group $COR^6$ wherein $R^6$ is hydrogen, halogen, hydroxy, or optionally substituted alkoxy, alkenyloxy, alkynyloxy, cycloalkoxy, aryloxy, alkylthio, alkenylthio, alkynylthio, arylthio, aminoxy, dialkyliminoxy or amino, or $R^6$ is a group $OR^7$ in which $R^7$ is an optionally substituted heterocyclic ring; or

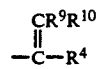

each of $R^9$ and $R^{10}$ being, independently, hydrogen or alkyl;
or a carboxylic acid salt of a compound with an equivalent amount of an inorganic or organic cation; have herbicidal properties. The invention also provides processes for their preparation and their use as herbicides.

12 Claims, No Drawings

HERBICIDAL COMPOUNDS

The present invention is concerned with triazine/-pyrimidine derivatives, processes for their preparation and their use as herbicides.

In the art a number of pyrimidine and triazine compounds are known to have herbicidal and plant growth regulatory activity.

Certain substituted pyrimidine compounds are described in East German Patent Specification No. 109170 as useful plant growth regulants, being able to regulate metabolic and growth process, for example promoting root formation and growth, encouraging fruit release and giving rise to dwarf features in plants.

Herbicidal compounds comprising a 2,4,6-substituted-1,3,5-triazine ring are well known, for example UK Patent No. 814947, which describes herbicidal compositions comprising certain 6-chloro-1,3,5-triazine-2,4-diamines and UK Patent No. 1132306 which describes certain 6-substituted 1,3,5-triazine 2,4-diamines, one of the amino groups having cyanoalkylamino substitution.

As part of a three part series of investigations on herbicides, the herbicidal and fungicidal properties of an extensive number of 2-substituted 4,6-dichloro-1,3,5-triazines Were reviewed by H. Koopman et al in Rec. Trav. Chim. 78, 967, (1959). Some 61 compounds were prepared and tested including methyl 2-(4,6-dichloro-1,3,5-triazin-2-yl)oxy-2-methyl acetic acid. The conclusion of the authors is that 2-alkoxy and 2-alkylthio 4,6-dichloro-1,3,5-triazines having 3–6 carbon atoms in the alkyl group have the most activity of all the compounds assessed, corresponding compounds having substituents in the alkyl group have nearly the same activity, and 2-aryloxy and 2-arylthio dichlorotriazines generally have no phytotoxic properties. The authors selected the 2-butoxy and 2-butylthio dichlorotriazine derivatives for field trials and examined the properties of various related 2-alkoxy and 2-alkylthio chlorotriazine compounds in later investigations reported in Rec. Trav. Chim. 79, 83, (1960).

EP-0 038 138 discloses the use of ethyl -[(4-amino-6-methyl-1,3,5-triazin-2-yl)oxy]propanoate in the preparation of certain herbicidal sulphonamides, but gives no indication of biological activity for that or related compounds.

A group of 2-(substituted methoxy)triazine/pyrimidine compounds has now been found which have a particularly useful herbicidal activity.

The present invention provides a compound of the general formula I

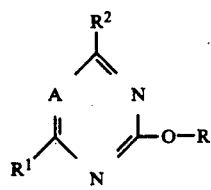
(I)

in which
A represents a nitrogen atom or a group $CR^5$;
$R^1$, $R^2$ and $R^5$ each independently represents a hydrogen or halogen atom, a formyl, cyano, carboxy or azido group, an optionally substituted alkyl, alkenyl, alkynyl, cycloalkyl, alkoxy, alkenyloxy, alkynyloxy, aryloxy, alkylthio, alkenylthio, alkynylthio, arylthio, alkylcarbonyl, alkoxycarbonyl, or dialkyliminoxy group, an unsubstituted aminoxy group or an amino or aminoxy group substituted by an alkyl group, itself optionally substituted by halogen, alkoxy, hydroxy or carboxy, an alkenyl group, an aryl group, a hydroxy group, a cyano group, an alkoxy group or an amino group itself optionally mono- or di- substituted by alkyl, aryl or alkylcarbonyl or which forms part of a heterocyclic ring;
and R represents a group

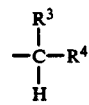

in which
$R^3$ represents a hydrogen atom, an optionally substituted alkyl, alkenyl, alkynyl, cycloalkyl, heterocyclic or aryl group, or a group $COR^8$ in which $R^8$ represents a hydroxy, alkoxy, carboxy, alkoxycarbonyl, amino or mono- or di- alkylamino group; and
$R^4$ represents a group $COR^6$ wherein $R^6$ represents a hydrogen or halogen atom, a hydroxy group, an optionally substituted alkoxy, alkenyloxy, alkynyloxy, cycloalkoxy, aryloxy, alkylthio, alkenylthio, alkynylthio, arylthio or dialkyliminoxy group or an amino or aminoxy group optionally substituted by an alkyl group, itself optionally substituted by halogen, alkoxy, hydroxy or carboxy, an alkenyl group, an aryl group, a hydroxy group, a cyano group, an alkoxy group or an amino group itself optionally mono- or di- substituted by alkyl, aryl or alkylcarbonyl or which forms part of a heterocyclic ring; or $R^6$ represents a group $OR^7$ in which $R^7$ represents an optionally substituted heterocyclic ring;
or R represents a group

in which $R^4$ is as defined above and $R^9$ and $R^{10}$ each independently represents a hydrogen atom or an alkyl group;
provided that when A represents a nitrogen atom, then $R^1$ and/or $R^2$ do not represent a chlorine atom;
or a carboxylic acid salt of a compound of general formula I with an equivalent amount of an inorganic or organic cation.

An alkyl, alkenyl or alkynyl radical or moiety may be a straight or branched chain group. Generally an alkyl radical or moiety has from 1 to 12 carbon atoms, preferably from 1 to 6, especially from 1 to 4, carbon atoms. Alkenyl and alkynyl radicals or moieties suitably have from 2 to 12 carbon atoms, preferably from 2 to 6, especially from 2 to 4, carbon atoms. Cycloalkyl groups suitably have from 3 to 8 carbon atom ring members.

An aryl radical, or an aryl moiety in an aralkyl, aryloxy or arylthio radical, may be a single or fused carbocyclic ring system having from 6 to 10 ring members. Suitably an aryl radical or moiety comprises a single ring system and preferably is a phenyl ring.

A heterocyclic radical is suitably a single or fused, saturated or unsaturated ring system having from 5 to 10, preferably 5 or 6, ring members of which from 1 to 3 ring members may be hetero atoms selected from oxygen, nitrogen and sulphur atoms.

Radicals represented by the symbols $R^1$, $R^2$, $R^3$, $R^5$, $R^6$ and $R^7$ may be unsubstituted or substituted. Where substituents are present, the substituent groups may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds. There may be one or more of the same or different substituents present in each radical.

Optional substituents for alkyl, alkenyl, alkynyl, alkoxy, alkenyloxy, alkynyloxy, alkylthio, alkenylthio, alkynylthio, alkylcarbonyl or alkoxycarbonyl groups may be independently selected from one or more of halogen atoms and alkoxy, alkenyloxy, aryloxy, hydroxy, alkylthio, arylthio, aryl, alkylsulphonyl, alkylsulphinyl, alkylenedioxy, alkylenedithio, haloalkyl and alkoxycarbonyl groups, heterocyclic groups, and dialkyliminoxy, optionally substituted amino, trialkylsilyl, alkylcarbonyl, arylcarbonyl, alkoxycarbonyl, carboxy, cyano, thiocyanato and optionally substituted aminocarbonyl groups.

Optional substituents for aryl, cycloalkyl aryloxy or arylthio groups or heterocyclic rings may be independently selected from one or more of halogen atoms and nitro, cyano, alkyl, hydroxyalkyl, haloalkyl, alkoxy, alkylthio, aryloxy, alkoxycarbonyl and aralkoxycarbonyl groups.

Optional substituents for an amino group or for an amino moiety in an aminocarbonyl group, suitably may be independently selected from alkyl, alkenyl, aryl, alkoxy, amino, mono- or di-alkylamino, arylamino, alkoxyalkyl, haloalkyl, hydroxy, hydroxyalkyl, cyano, carboxyalkyl or alkylcarbonylamino, or the amino group may form part of a heterocyclic ring.

An alkyl radical or moiety when present as a substituent or as part of a substituent group, preferably has from 1 to 4 carbon atoms, especially 1 or 2 carbon atoms. A haloalkyl radical suitably has from 1 to 3 halogen atoms and a preferred haloalkyl radical is a trifluoromethyl group. As a substituent an alkenyl moiety suitably has from 2 to 4 carbon atoms. An aryl radical when present as a substituent is preferably a phenyl group. A halogen atom as a substituent is suitably a fluorine, chlorine or bromine atom.

Carboxylic acid salts of the compounds of general formula I include salts with inorganic cations derived from alkali metals, alkaline earth metals such as, for example, sodium, potassium, calcium and magnesium, and transition metals, for example copper, and with organic cations such as alkylammonium and alkylsulphonium cations. A preferred carboxylic acid salt is a sodium salt.

A is preferably a nitrogen atom or a group CH.

Suitable examples of the radicals $R^1$ and $R^2$ include halogen atoms, $C_{1-4}$ alkyl groups, $C_{1-4}$ alkoxy groups, $C_{1-4}$ alkylthio groups, and mono- and di-$(C_{1-4})$ alkylamino groups. Preferably $R^1$ and $R^2$ are independently selected from chlorine atoms, methyl groups, methoxy groups, methylthio groups, methylamino groups and dimethylamino groups.

The group R may be a group of the formula

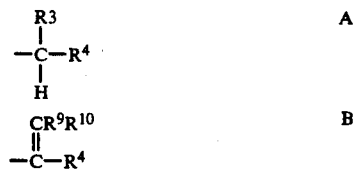

In the latter group one of $R^9$ and $R^{10}$ is suitably a hydrogen atom and the other a $C_{1-4}$ alkyl group, preferably a methyl group. Preferably R represents a group of the formula —$CHR^3R^4$.

Suitable examples of the radical $R^3$ include optionally substituted $C_{1-6}$ alkyl, $C_{2-6}$ alkenyl, $C_{2-6}$ alkynyl, $C_{3-6}$ cycloalkyl, phen($C_{1-4}$)alkyl, phenyl groups and 5 or 6 membered heterocyclic groups, for example derived from thiophene. The radical $R^3$ may suitably represent a hydrogen atom; a $C_{1-6}$ alkyl group optionally substituted by a $C_{1-4}$ alkylthio group; a cyclohexyl group; a benzyl group; a phenyl group optionally substituted by one or more substituents independently selected from halogen atoms, trifluoromethyl groups, $C_{1-4}$ alkyl groups and ($C_{1-4}$alkoxy)carbonyl groups; a thienyl group; a carboxy group; a ($C_{1-4}$alkoxy)carbonyl group; a ($C_{1-4}$alkoxy)carbonylcarbonyl group or a di($C_{1-4}$alkyl)carbamoyl group.

Preferably the radical $R^3$ is selected from $C_{2-6}$ alkyl groups, especially $C_2$-$C_4$ alkyl groups, benzyl groups and unsubstituted phenyl groups. Especially preferred compounds are those in which the group $R^3$ is an isopropyl, n-propyl, i-butyl, n-butyl, s-butyl, t-butyl, benzyl or phenyl group.

As suitable examples of the radical $R^4$, there may be mentioned groups $COR^6$ in which $R^6$ represents a hydrogen atom, a halogen atom, for example chlorine, a hydroxy group or an optionally substituted $C_{1-6}$ alkoxy, $C_{2-6}$ alkenyloxy, $C_{2-6}$ alkynyloxy, $C_{3-6}$ cycloalkyloxy, $C_{1-6}$ alkylthio, $C_{2-6}$ alkenylthio, $C_{2-6}$ alkynylthio, phenyl, phenoxy, phenylthio, di($C_{1-4}$alkyl)aminoxy, di($C_{1-4}$alkyl)iminoxy or amino groups, and groups $COOR^7$ in which $R^7$ represents an optionally substituted 5 or 6 membered heterocyclic ring having from 1 to 3 hetero atoms in the ring.

The radical $R^4$ may suitably represent a group $COR^6$ in which $R^6$ represents a hydroxy group; a $C_{1-4}$ alkoxy group optionally substituted by a halogen atom or a $C_{1-4}$ alkoxy, $C_{1-4}$ alkylthio, phenyl, benzyl itself optionally substituted on the phenyl ring by one or more substituents independently selected from halogen atoms and $C_{1-4}$ alkoxy groups, furyl, tetrahydrofuryl or thienyl group; a $C_{1-4}$ alkylthio group; a $C_{2-4}$ alkynyloxy group; a phenoxy group optionally substituted by one or more substituents independently selected from $C_{1-4}$ alkyl groups, nitro groups and hydroxy($C_{1-4}$)alkyl groups; a phenylthio group; an amino group optionally substitued by an amino group, a di($C_{1-4}$)alkylamino group or a phenyl group optionally substituted by a carboxy or ($C_{1-4}$ alkoxy)carbonyl group; or a di($C_{1-4}$)alkylaminoxy group. In the case of a phenoxy group $R^6$ the phenyl ring may also be substituted by a group

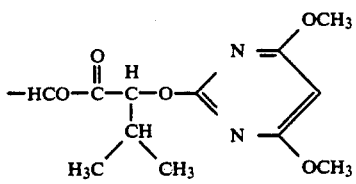

$R^4$ preferably represents the group $COR^6$ in which $R^6$ represents a hydroxy group or a $C_{1-4}$ alkoxy group.

It will be appreciated that the compounds of the present invention in which $R^3$ is other than a hydrogen atom have an asymmetric carbon atom and will therefore exist in different stereoisomeric forms. The present invention is to be understood to include all the various isomeric forms of the compounds of general formula I and mixtures thereof in whatever proportion. Thus the R- and S-enantiomers of the compound of general formula IA

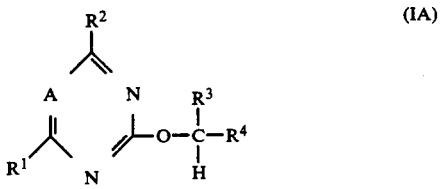

in which $R^3$ is other than a hydrogen atom, and mixtures thereof are included within the present invention.

The present invention further provides a process for the preparation of a compound of the present invention, which process comprises
a) reacting a compound of the general formula II

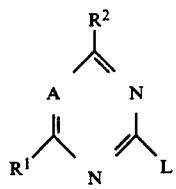

in which $R^1$, $R^2$ and A are as defined above and L represents a leaving group, with a compound of the general formula III

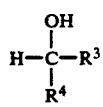

in which $R^3$ and $R^4$ are as defined above, or
b) for compounds in which A represents $CR^5$, reacting a compound of the general formula IV

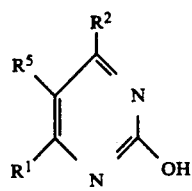

in which $R^1$, $R^2$ and $R^5$ are as defined above, with a compound of the general formula V

in which $R^3$ and $R^4$ are as defined above, and X represents a leaving group, and, if required or desired, converting a compound of general formula I into another compound of general formula I, or converting a carboxylic acid of general formula I into a salt thereof, or converting a carboxylic acid salt of a compound of general formula I into the free acid or into another salt.

A leaving group is any group that will, under the reaction conditions, cleave from the starting material thus promoting reaction at a specified site.

The leaving group L in a compound of general formula II is conveniently a halogen atom, for example a bromine, chlorine or iodine atom, or, especially for the pyrimidine starting materials, an alkanesulphonyl group, for example methanesulphonyl.

The leaving group X in a compound of general formula V is suitably a halogen atom or a sulphonyloxy group, for example a methanesulphonyloxy or tosyloxy group. Halogen atoms represented by X include, conveniently, chlorine, bromine or iodine atoms. X is, however, preferably a bromine atom.

It is preferred that reaction (a) or reaction (b) is carried out under basic conditions. The basic conditions may suitably be provided, for example, by an alkali metal hydride, such as sodium or potassium hydride, an alkaline earth metal hydride, such as calcium hydride, an alkali metal carbonate or bicarbonate, such as sodium or potassium carbonate or sodium bicarbonate, an alkali metal alkoxide, such as potassium t-butoxide, an alkali metal hydroxide, such as sodium or potassium hydroxide, or a tertiary amine, such as triethylamine, pyridine or 1,8-diazabicyclo[5.4.0]undec-7-ene.

The reaction (a) or (b) is suitably carried out in an inert organic solvent such as a hydrocarbon solvent, eg. benzene or toluene, a chlorinated hydrocarbon, eg. dichloromethane or chloroform, an alcohol, eg. methanol or ethanol, an ether, eg. diethyl ether, tetrahydrofuran, 1,4-dioxane, a ketone, eg. acetone or methyl ethyl ketone, an ester, eg. ethyl acetate, an aprotic polar solvent, eg. dimethylformamide, dimethylacetamide or dimethylsulphoxide or a nitrile, eg. acetonitrile, or in water, with appropriate selection of the agent generating the basic conditions for the reaction.

The reaction (a) or (b) may be used to prepare compounds of the formula I for both meanings of R. Compounds in which R is of formula B are suitably prepared using a starting material of formula III or V in which $R^3$ is an alk-1-enyl group.

Either reaction may be carried out over a wide temperature range, for example from 0° C. to the reflux temperature of the solvent employed.

The amounts of reactants II and III may vary suitably within the range of 0.1 to 10 moles of II per mole of III. However substantially equimolar amounts of II and III are preferably employed. Similarly the amount of reactants IV and V may be in the range of from 0.1 to 10 moles of IV per mole of V, but preferably equimolar amounts of IV and V are used.

The enantiomers of the compounds of general formula I may, of course, be prepared from the corresponding optically active enantiomer starting material of general formula III or V by either process of the present invention, or by resolution of a mixture of optical isomers. In the preparation of enantiomers of compounds I in which $R^3$ is aryl, it is most advantageous to employ optically active starting materials III or V which are in the form of an acid, i.e. in which $R^4$ is COOH, and, if desired, converting the resulting optically active compound I into the corresponding ester derivative.

The compound of general formula I obtained by either of the methods (a) or (b) may readily be converted to a further compound of general formula I by methods known to those skilled in the art. Thus for example, a compound of general formula I where $R^1$ and/or represents $R^2$ is a halogen atom, suitably chlorine, may be transformed into other derivatives by nucleophilic displacement, for example by reaction with an amine, such as dimethylamine, to give the corresponding compound of general formula I in which $R^1$ and/or $R^2$ represents a substituted amino group. Likewise a compound of general formula I in which $R^1$ and/or $R^2$ represents a halogen atom, may be reacted with an alkylthio organo-metallic compound, for example sodium methanethiolate, to yield the corresponding compound of general formula I in which $R^1$ and/or $R^2$ represents an alkylthio group such as methylthio, or may be hydrogenated to yield the corresponding compound in which $R^1$ and/or $R^2$ is a hydrogen atom. Compounds of general formula I in which $R^4$ represents an ester group may be hydrolysed by methods well known in the art to yield acids of formula I. Alternatively, hydrogenation of, for example, the benzyl ester of formula I can be employed to yield acids of formula I.

Acid and salt conversion reactions may be carried out using conventional methods as appropriate.

The prepared compounds of general formula I may, if desired, be isolated and purified using conventional techniques.

The starting triazine compounds of general formula II (i.e. in which A is a nitrogen atom) are either known or can be prepared using techniques described in the literature. For example such compounds may be prepared from 2,4,6-trichlorotriazine by methods such as those described by Dudley et al, J. Am. Chem. Soc., 73, 2986, (1951), Koopman et al, Rec. Trav. Chim., 79, 83, (1960), Hirt et al, Helv. Chim. Acta, 33, 1365, (1950), Kobe et al, Monatshefte fur Chemie, 101, 724, (1970) and Ross et al, US Patent Specification No. 3 316 263.

The starting pyrimidines of general formulae II and IV may be prepared by conventional techniques, for example those described in Heterocyclic Compounds, 16 "The Pyrimidines", edited by D.J. Brown, Interscience, 1962.

The compounds of general formula III are either known compounds or may be prepared by conventional procedures. Compounds in which $R^3$ represents an aryl group may for example be prepared by treating the corresponding aldehyde, $R^3$CHO, with a suitable cyanide compound, for example potassium cyanide or trimethylsilylcyanide with, respectively, zinc iodide or sodium bisulphite, followed by conversion of the cyano substituent to a group $R^4$, see, for example, Schnur and Morville, J.Med. Chem. 29, 770 (1986) and U.S. Patent Specification No. 4537623. Compounds in which $R^3$ represents an alkyl group may, for example, be prepared by the method of Kolasa and Miller, J. Org. Chem. 52, 4978, (1987), starting from a suitable amino acid with a 2 stage conversion.

The compounds of general formula V may be prepared by conventional techniques, for example by halogenating a corresponding compound, for example by the procedure of Epstein et al. J.Med. Chem., 24, 481, (1981).

Compounds of the general formula I have been found to have interesting activity as herbicides having a wide range of pre- and post-emergence activity against undesirable species.

The present invention therefore provides a herbicidal composition which comprises a compound of the present invention in association with a carrier.

Preferably there are at least two carriers in a composition of the present invention, at least one of which is a surface-active agent.

The present invention further provides the use of a compound according to the invention as a herbicide.

Further, in accordance with the invention there is provided a method of combating undesired plant growth at a locus by treating the locus with a composition or compound according to the invention. The locus may, for example, be the soil or plants in a crop area. Application to the locus may be pre-emergence or post-emergence. The dosage of active ingredient used may, for example, be from 0.01 to 10kg/ha, preferably 0.05 to 4kg/ha.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ether; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution.

Thus preferably at least one carrier in a composition according to the invention is a surface-active agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may also contain other ingredients, for example other compounds possessing herbicidal properties or compounds possessing fungicidal or insecticidal properties.

The following Examples illustrate the invention.

EXAMPLE 1

Methyl 2-(4,6-dimethylpyrimidin-2-yl)oxy-3-methyl butanoate a) 2-Acetoxy-3-methylbutanoic acid Into 300ml of glacial acetic acid there was stirred 11.7g (0.1 moles) of dl-valine. 13.8g of sodium nitrite was added, with stirring, over the duration of 1 hour and the temperature of the reaction medium maintained at room temperature by means of a water bath. After the mixture had been stirred overnight at room temperature, the acetic acid was evaporated off and water (50ml) added. Solvent extraction using diethyl ether then followed. The diethyl ether portion was washed with water, dried over anhydrous magnesium sulphate and the ether evaporated off to yield 12.2g of the title product as a colourless oil.

b) Methyl 2-hydroxy-3-methylbutanoate 11.2g (0.09 moles) of the product of (a) was introduced into 160ml of absolute methanol and the solution cooled to −40° C. 5.7ml (0.099 moles) of thionyl chloride was added dropwise in the course of 30 minutes whilst stirring at −40° C. and allowed to warm to room temperature overnight. After evaporating the reaction mixture to dryness, the title product was obtained (7.7g; yield 65%) as a pale oil. c) Methyl 2-(4,6-dimethylpyrimidin-2-yl)oxy-3-methylbutanoate 1.5g of the product of (b) and 2.11g (0.011 moles) of 4,6-dimethyl-2-methanesulphonyl pyrimidine were dissolved in 20ml acetone. 1.6g of potassium carbonate were added and the reaction mixture refluxed for 4 hours. Following thin layer chromatography to establish that the reaction had reached completion, the mixture was evaporated to dryness and 10ml water added. Solvent extraction using chloroform followed and the chloroform extracts were dried over anhydrous sodium sulphate and the solvent evaporated off. The oil resulting was subjected to flash column chromatography using ethyl acetate: hexane (1:1) as eluant to yield 1.1g (yield 42%) of the title compound as a colourless oil.

Analysis (%): Calc. C 60.5. H 7.6. N 11.8. Found C 60.3. H 7.9. N 11.7.

NMR δ(CDCl$_3$) 6.65 (1H,s), 5.01 (1H,d), 3.7 (3H,s), 2.46 (6H,s), 2.40 (1H,m), 1.10 (6H,dd) ppm.

EXAMPLE 2

2-(4,6-Dimethylpyrimidin-2-yl)oxy,3-methylbutanoic acid 0.8g (3.36mmol) of the butanoate prepared in Example 1, was dissolved in 8ml of absolute methanol to which 8ml of an aqueous solution (10% by volume) of sodium hydroxide was then added. The reaction mixture was stirred overnight at room temperature. Thin layer chromatography confirmed that the reaction was complete. The methanol was then evaporated off and 5ml water added. Concentrated hydrochloric acid was added to the mixture, whilst cooling, to bring the solution to a pH of 2. Two aliquots of chloroform were used to extract the product of the reaction. The extracts were dried over anhydrous sodium sulphate and then subjected to evaporation to yield 0.7g of an oily solid. Following trituration with 5ml of diethyl ether, 0.5g (yield 66% by weight) of a colourless solid was obtained.

Melting point: 131.8° C.

Analysis (%): Calc. C 58.9. H 7.1. N 12.5. Found C 59.1. H 7.2. N 12.7.

EXAMPLE 3

Methyl 2-(4,6-dimethoxypyrimidin-2-yl)oxy,2-phenyl acetate

A mixture of 4,6-dimethoxy-2-methanesulphonyl-pyrimidine (4.3g, 20mmol), methyl mandelate (3.3g, 20mmol) and potassium carbonate (2.76g, 20mmol) in 100ml methyl ethyl ketone was refluxed for 3 hours. After evaporating off the methyl ethyl ketone solvent, 200ml of water were added to the mixture and a precipitate formed. 5.02g (yield 83% by weight) of the title compound were obtained following filtration and drying of the precipitate.

Melting point: 100.6° C.

Analysis (%) : Calc. C 59.2. H 5.3. N 9.2. Found C 58.6. H 5.3. N 9.3.

EXAMPLE 4

2-(4,6-Dimethoxypyrimidin-2-yl)oxy,2-phenylacetic acid

A mixture of 1.22g (4mmol) of the ester prepared in Example 3 and 0.16g (4mmol) of sodium hydroxide in 20 ml methanol was stirred for 2 hours at 0° C. and then overnight at room temperature. Thin layer chromatography indicated the reaction to be virtually complete. The methanol was then evaporated off in vacuo and an additional 50ml of water was added. The aqueous phase was made slightly acidic with dilute hydrochloric acid and the resulting precipitate was filtered off and dried. Following purification by recrystallisation from ethyl acetate/hexane, 0.65g (yield 56% by weight) of the title compound was obtained.

Melting point : 159.0° C.

Analysis (%) : Calc. C 57.9. H 4.8. N 9.7. Found C 58.4. H 4.9. N 10.0.

EXAMPLE 5

Methyl 2-(4,6-dimethoxy-1,3,5-triazin-2-yl)oxy,3methylbutanoate 2 00g (0.011mol) of 2-chloro-4,6-dimethoxytriazine, 1.5g of methyl 2-hydroxy-3-methyl butanoate, 1.73g (0.013mol) of potassium carbonate in 50ml of methyl ethyl ketone wer refluxed overnight. When the reaction was complete, as determined by thin layer chromatography, the potassium carbonate was filtered off and the solvent evaporated off to leave a yellow solid (2.38g). Flash column chromatography yielded the pure product as a pale yellow oil (1.93g, yield 65% by weight).

Analysis (%): Calc. C 48.7. H 6.3. N 15.5. Found C47.1. H5.8. N17.0.

NMR $\delta$(CDCl$_3$) 5.08 (1H,d), 3.98 (6H,s), 3.72 (3H,s), 2.30 (1H,m), 1.07 (6H,dd) ppm

EXAMPLE 6

Ethyl 2-(4,6-dimethoxytriazin-2-yl)oxy,2-phenyl acetate

2-Chloro-4,6-dimethoxytriazine (1.75g), ethyl mandelate (1.8g) and potassium carbonate (1.5g) in methyl ethyl ketone (75ml) were stirred and heated at reflux overnight. The reaction mixture was cooled to room temperature, concentrated and the residue poured into water. The precipitated product was filtered off, washed with water and then dried to give 2.6g (81.5% by weight yield) of the title compound. Melting point: 92° C.

Analysis (%): Calc. C 56.4. H 5.4. N 13.2. Found C 57.0. H 5.4. N 13.0.

EXAMPLE 7

Ethyl 2-(4,6-dimethylpyrimidin-2-yl)oxyacetate

2-Hydroxy-4,6-dimethyl pyrimidine (10g, 0.08 mol) was dissolved in 150ml of dimethylformamide. Ethyl bromoacetate (13.5g, 0.08 mol) was added and also, subsequently, 11.1g of potassium carbonate. The reaction mixture was refluxed overnight. A precipitate had formed which was filtered off and the solvent was then evaporated off from the filtrate to form a crude oily product. Following purification by flash chromatography, 4.5g of the title product were obtained in the form of a red oil.

Analysis (%): Calc. C 57.1. H 6.7. N 13.3. NMR $\delta$(CDCl$_3$) 6.68 (1H,s), 4.87 (2H,s), 4.20 (2H,q), 2.37 (6H,s), 1.22 (3H,t) ppm.

EXAMPLE 8

2-(4,6-Dimethylpyrimidin-2-yl)oxyacetic acid 2g (9.5mmol) of the ethyl ester prepared in Example 7 were dissolved in 20ml of ethanol. 25ml of an aqueous solution (10% by vol) of sodium hydroxide were then added to the solution. The reaction mixture was refluxed for 4 hours. After the reaction was complete, as confirmed by thin layer chromatography, the ethanol was evaporated off, the aqueous residue cooled, acidified to a pH of 2 and the product extracted into chloroform. Following drying first over anhydrous sodium sulphate and then by evaporation, 0.6g (yield 35% by weight) of a reddish oil were obtained which oil crystallised on standing.

Melting point: 72° C.

Analysis (%): Calc. C 52.7. H 5.5. N 15.4. Found C 48.6. H 5.6. N 13.4.

NMR $\delta$(CDCl$_3$) 6.70 (1H,s), 6.51 (1H, broad s), 4.93 (2H,s), 2.48 (6H,s) ppm

EXAMPLE 9

Ethyl 2-(4,6-dimethylpyrimidin-2-yloxy),2-phenyl acetate

A mixture of 2-hydroxy-4,6-dimethylpyrimidine (5.60g, 50mmol), ethyl 2-bromo,2-phenylacetate (12.15g, 50mmol) and potassium carbonate (6.90g, 50 mmol) in 250 ml of methyl ethyl ketone was refluxed overnight. The solvent was evaporated off, water was added to the remaining mixture and the whole extracted into diethyl ether. Following drying over anhydrous magnesium sulphate and evaporation, the crude product was purified by flash column chromatography to give 4.8 g (34% by weight yield) of the title compound in the form of an oil.

Analysis (%): Calc. C 67.1. H 6.3. N 9.8. Found C 67.4. H 6.5. N 9.4.

EXAMPLE 10

2-(4,6-Dimethylpyrimidin-2-yl)oxy,2-phenylacetic acid 3.60g (12.6mmol) of the ethyl ester prepared in Example 9 were added to a stirred solution of sodium hydroxide (0.504g, 12.6mmol) in a mixture of ethanol (20ml) and water (20ml) at 0° C. After stirring for 2-3 hours at 0° C., the mixture was allowed to warm gradually to room temperature and then stirred overnight. Approximately 300ml of water was added and the mixture was made slightly acidic with dilute hydrochloric acid. The precipitate that formed was filtered off and dried by suction. 2.4g (74% by weight yield) of the title compound was obtained following recrystallisation from hexane/ethyl acetate.

Melting point: 148.4° C.

Analysis (%): Calc. C 65.1. H 5.4. N 10.9. Found C 64.7. H 5.5. N 11.5.

EXAMPLE 11

2-(4,6-Dimethoxytriazin-2-yl)oxy,2-phenylacetic acid 1.22g (4.0mmol) of the ester methyl 2-(4,6-dimethoxytriazin-2-yl)oxy, 2-phenyl acetate (prepared in analogous manner to the corresponding ethyl ester as described in Example 6) was added to a stirred solution of 0.16g (4.0mmol) of sodium hydroxide in a mixture of water (20ml) and methanol (20ml). The mixture was refluxed for 1 hour after which time the reaction was complete, as confirmed by thin layer chromatography. The methanol was removed from the solution by evaporation in vacuo and 50ml water added to the remaining liquid. A precipitate formed which was filtered off, washed and dried to give 0.73g (yield 63% by weight) of the title compound.

Melting point: 128.2° C.

Analysis (%): Calc. C 53.6. H 4.5. N 14.4. Found C 53.2. H 4.6. N 14.5.

EXAMPLES 12 TO 163

Further compounds of the general formula

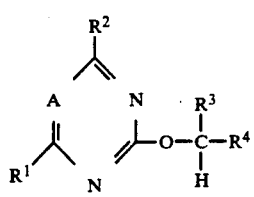

were prepared in analogous manner to the procedures described in Examples 1 to 11 above except for the compounds of Examples Nos. 159 to 162 which were prepared from the corresponding benzyl esters (the compounds of Examples 155 to 158) by the conventional procedure of hydrogenation at room temperature and pressure using palladium/charcoal powder and ethanol as solvent. Details of the compounds prepared are given in Table I below. In the Table, the designation "N/A" stands for "not available".

TABLE 1

| Example | A | $R^1$ | $R^2$ | $R^3$ | $R^4$ | Melting Point (°C.) | Analysis (%) Calc Found C | H | N |
|---|---|---|---|---|---|---|---|---|---|
| 12 | N | $OCH_3$ | $OCH_3$ | $C_6H_5$ | $CO_2CH_3$ | 91.5 | 55.1 / 55.5 | 4.9 / 4.9 | 13.8 / 13.8 |
| 13 | CH | $CH_3$ | $CH_3$ | 2-$ClC_6H_4$ | $CO_2C_2H_5$ | 72-75 | 59.9 / 58.9 | 5.3 / 5.2 | 8.7 / 8.4 |
| 14 | N | $OCH_3$ | $OCH_3$ | 2-$FC_6H_4$ | $CO_2CH_3$ | 93 | 52.0 / 51.5 | 4.4 / 4.6 | 13.0 / 12.2 |
| 15 | CH | $OCH_3$ | $OCH_3$ | 2-$FC_6H_4$ | $CO_2CH_3$ | 90-92 | 55.9 / 56.0 | 4.7 / 4.8 | 8.7 / 8.6 |
| 16 | N | $OCH_3$ | $OCH_3$ | 3-$CF_3C_6H_4$ | $CO_2CH_3$ | oil | 48.3 / 48.7 | 3.8 / 4.0 | 11.3 / 11.1 |
| 17 | CH | $OCH_3$ | $OCH_3$ | 3-$CF_3C_6H_4$ | $CO_2CH_3$ | 96-99 | 51.6 / 51.5 | 4.1 / 4.1 | 7.5 / 7.7 |
| 18 | CH | $CH_3$ | $CH_3$ | 2-$(CO_2CH_3)C_6H_4$ | $CO_2CH_3$ | oil | 61.8 / 61.2 | 5.5 / 5.7 | |
| 19 | CH | $OCH_3$ | $OCH_3$ | 2,6-$diClC_6H_3$ | $CO_2CH_3$ | 169-170 | 48.3 / 48.7 | 3.8 / 3.9 | 7.5 / 7.4 |
| 20 | CH | $OCH_3$ | $OCH_3$ | $CH_2C_6H_5$ | $CO_2CH_3$ | oil | 60.4 / 60.3 | 5.7 / 5.8 | 8.8 / 8.7 |
| 21 | N | $OCH_3$ | $OCH_3$ | $CH_2C_6H_5$ | $CO_2CH_3$ | oil | 56.4 / 56.4 | 5.4 / 5.5 | 13.2 / 12.8 |
| 22 | CH | $OCH_3$ | $OCH_3$ | $CH_2C_6H_5$ | COOH | 113.5 | 59.3 / 58.4 | 5.3 / 5.3 | 9.2 / 9.1 |
| 23 | N | $OCH_3$ | Cl | $CH_2C_6H_5$ | $CO_2CH_3$ | oil | 51.9 / 51.3 | 4.3 / 4.4 | 13.0 / 12.9 |
| 24 | N | $OCH_3$ | $N(CH_3)_2$ | $CH_2C_6H_5$ | $CO_2CH_3$ | 61-62 | 57.8 / 58.2 | 6.0 / 6.0 | 16.9 / 17.1 |
| 25 | N | $OCH_3$ | $NHCH_3$ | $CH_2C_6H_5$ | $CO_2CH_3$ | 62-64 | 56.6 / 56.0 | 5.7 / 5.7 | 17.6 / 17.8 |
| 26 | N | $OCH_3$ | $SCH_3$ | $CH_2C_6H_5$ | $CO_2CH_3$ | oil | 53.7 / N/A | 5.1 / N/A | 12.5 / N/A |
| 27 | CH | Cl | $OCH_3$ | $C_6H_5$ | $CO_2CH_3$ | 72.4 | 54.5 / 54.7 | 4.2 / 4.3 | 9.1 / 9.3 |
| 28 | CH | $OCH_3$ | $SCH_3$ | $C_6H_5$ | $CO_2CH_3$ | 93.95 | 56.2 / 55.8 | 5.0 / 5.1 | 8.7 / 9.1 |
| 29 | CH | $OCH_3$ | $OCH_3$ | 2-thienyl | $CO_2CH_3$ | 118-120 | 50.3 / 50.4 | 4.6 / 4.6 | 9.0 / 8.8 |
| 30 | CH | $CH_3$ | $OCH_3$ | $C_6H_5$ | $CO_2CH_3$ | 70.7 | 62.5 / 62.8 | 5.6 / 5.7 | 9.7 / 9.7 |
| 31 | CH | $OCH_3$ | $OCH_3$ | $C_6H_5$ | COOH(S) | 137-140 | 57.9 / 57.5 | 4.9 / 5.0 | 9.7 / 9.5 |
| 32 | CH | $OCH_3$ | $OCH_3$ | $C_6H_5$ | COOH(R) | 133 | 57.9 / 58.1 | 4.9 / 5.1 | 9.7 / 10.0 |
| 33 | CH | $OCH_3$ | $OCH_3$ | $C_6H_5$ | $CO_2CH_3$(S) | 95 | 59.2 / 59.0 | 5.3 / 5.3 | 9.2 / 9.1 |
| 34 | CH | $OCH_3$ | $OCH_3$ | $C_6H_5$ | $CO_2CH_3$(R) | 92-94 | 59.2 / 59.4 | 5.3 / 5.4 | 9.2 / 9.1 |
| 35 | CH | $CH_3$ | $CH_3$ | $C_6H_5$ | $CO_2CH_3$ | 68.2 | 66.2 / 66.3 | 5.9 / 6.1 | 10.3 / 10.1 |
| 36 | N | $OCH_3$ | $N(CH_3)_2$ | $C_6H_5$ | $CO_2CH_3$ | 103.5 | 56.6 / 56.7 | 5.7 / 5.8 | 17.6 / 17.5 |
| 37 | CH | $OCH_3$ | $OCH_3$ | $C_6H_5$ | $COO^-Na^+$ | 242-243 | 53.9 / 52.4 | 4.2 / 4.3 | 9.0 / 8.9 |
| 38 | N | $OCH_3$ | $NHCH_3$ | $C_6H_5$ | $CO_2CH_3$ | 112.2 | 55.3 / 55.6 | 5.3 / 5.5 | 18.4 / 18.1 |
| 39 | N | $N(CH_3)_2$ | $CH_3$ | $C_6H_5$ | $CO_2CH_3$ | 133.2 | 59.6 / 59.4 | 6.0 / 6.0 | 18.5 / 18.4 |
| 40 | N | $CH_3$ | $OCH_3$ | $C_6H_5$ | $CO_2CH_3$ | 72 | 58.1 / 59.0 | 5.2 / 5.2 | 14.5 / 14.7 |
| 41 | CH | $CH_3$ | $CH_3$ | $CH_3$ | $CO_2CH_3$ | oil | 57.1 / N/A | 6.7 / N/A | 13.3 / N/A |
| 42 | CH | $CH_3$ | $CH_3$ | $CH_3$ | COOH | 117 | 55.1 | 6.1 | 14.3 |

TABLE 1-continued

| Example | A | R¹ | R² | R³ | R⁴ | Melting Point (°C.) | Analysis (%) Calc / Found C | H | N |
|---|---|---|---|---|---|---|---|---|---|
| | | | | | | | 46.5 | 6.3 | 14.3 |
| 43 | CH | CH₃ | CH₃ | C₂H₅ | CO₂CH₃ | oil | 58.9 | 7.1 | 12.5 |
| | | | | | | | 58.7 | 7.2 | 12.0 |
| 44 | CH | CH₃ | CH₃ | C₂H₅ | COOH | 112.5 | 57.1 | 6.7 | 13.3 |
| | | | | | | | 57.1 | 6.8 | 13.1 |
| 45 | CH | CH₃ | CH₃ | iC₄H₉ | CO₂CH₃ | oil | 61.9 | 7.9 | 11.1 |
| | | | | | | | 63.3 | 8.3 | 10.7 |
| 46 | CH | CH₃ | CH₃ | iC₄H₉ | COOH | 111.9 | 60.5 | 7.6 | 11.8 |
| | | | | | | | 59.7 | 7.5 | 12.2 |
| 47 | CH | CH₃ | CH₃ | sC₄H₉ | CO₂CH₃ | oil | 61.9 | 7.9 | 11.1 |
| | | | | | | | 58.9 | 7.8 | 9.7 |
| 48 | CH | CH₃ | CH₃ | sC₄H₉ | COOH | 115.0 | 60.5 | 7.6 | 11.8 |
| | | | | | | | 60.9 | 8.0 | 11.1 |
| 49 | CH | CH₃ | CH₃ | nC₃H₇ | CO₂CH₃ | oil | 60.5 | 7.5 | 11.8 |
| | | | | | | | 58.8 | 7.4 | 11.2 |
| 50 | CH | CH₃ | CH₃ | tC₄H₉ | CO₂CH₃ | oil | 61.9 | 7.9 | 11.1 |
| | | | | | | | 59.2 | 8.0 | 10.1 |
| 51 | CH | CH₃ | CH₃ | nC₄H₉ | CO₂CH₃ | oil | 61.9 | 7.9 | 11.1 |
| | | | | | | | N/A | N/A | N/A |
| 52 | CH | OCH₃ | OCH₃ | CH₃ | COOH | 144 | 47.4 | 5.3 | 12.3 |
| | | | | | | | 44.4 | 4.9 | 12.5 |
| 53 | CH | OCH₃ | OCH₃ | C₂H₅ | COOH | 122 | 49.6 | 5.8 | 11.6 |
| | | | | | | | 47.6 | 5.9 | 11.1 |
| 54 | CH | OCH₃ | OCH₃ | iC₃H₇ | COOH | 133.5 | 51.6 | 6.3 | 10.9 |
| | | | | | | | 51.6 | 6.2 | 11.1 |
| 55 | CH | OCH₃ | OCH₃ | iC₄H₉ | CO₂CH₃ | oil | 54.9 | 7.0 | 9.9 |
| | | | | | | | 55.0 | 7.1 | 10.0 |
| 56 | CH | OCH₃ | OCH₃ | iC₃H₇ | CO₂CH₃ | 48.4 | 53.3 | 6.7 | 10.4 |
| | | | | | | | 53.8 | 7.1 | 10.8 |
| 57 | CH | OCH₃ | OCH₃ | iC₄H₉ | COOH | 116 | 53.3 | 6.7 | 10.4 |
| | | | | | | | 52.9 | 6.7 | 10.4 |
| 58 | CH | OCH₃ | OCH₃ | sC₄H₉ | CO₂CH₃ | 42 | 54.9 | 7.0 | 9.9 |
| | | | | | | | 54.8 | 7.5 | 9.5 |
| 59 | CH | OCH₃ | OCH₃ | sC₄H₉ | COOH | 96.2 | 53.3 | 6.7 | 10.4 |
| | | | | | | | 53.9 | 6.9 | 10.5 |
| 60 | CH | OCH₃ | OCH₃ | nC₃H₇ | CO₂CH₃ | 60.5 | 53.3 | 6.7 | 10.4 |
| | | | | | | | 53.3 | 6.8 | 10.4 |
| 61 | CH | OCH₃ | OCH₃ | nC₃H₇ | COOH | 114 | 51.6 | 6.3 | 10.9 |
| | | | | | | | 51.5 | 6.5 | 10.7 |
| 62 | CH | OCH₃ | OCH₃ | tC₄H₉ | CO₂CH₃ | 104.5 | 54.9 | 7.0 | 9.9 |
| | | | | | | | 54.4 | 6.9 | 9.6 |
| 63 | N | OCH₃ | OCH₃ | CH₃ | CO₂CH₃(R) | oil | 44.4 | 5.3 | 17.3 |
| | | | | | | | 44.5 | 5.4 | 17.8 |
| 64 | N | OCH₃ | OCH₃ | CH₃ | CO₂CH₃(S) | oil | 44.4 | 5.3 | 17.3 |
| | | | | | | | 45.4 | 5.6 | 16.9 |
| 65 | N | OCH₃ | OCH₃ | C₂H₅ | CO₂CH₃ | oil | 46.7 | 5.8 | 16.3 |
| | | | | | | | 44.6 | 5.6 | 14.8 |
| 66 | N | OCH₃ | OCH₃ | iC₄H₉ | CO₂CH₃ | oil | 50.5 | 6.7 | 14.7 |
| | | | | | | | 51.5 | 7.0 | 11.8 |
| 67 | N | OCH₃ | OCH₃ | nC₃H₇ | CO₂CH₃ | oil | 48.7 | 6.3 | 15.5 |
| | | | | | | | 48.8 | 6.7 | 15.4 |
| 68 | CH | OCH₃ | OCH₃ | tC₄H₉ | COOH | 167.5 | 53.3 | 6.7 | 10.4 |
| | | | | | | | 53.2 | 6.8 | 10.5 |
| 69 | CH | OCH₃ | OCH₃ | nC₄H₉ | CO₂CH₃ | oil | 54.9 | 7.0 | 9.9 |
| | | | | | | | 51.3 | 6.6 | 9.4 |
| 70 | CH | OCH₃ | OCH₃ | nC₄H₉ | COOH | 113.7 | 53.3 | 6.7 | 10.4 |
| | | | | | | | 53.6 | 6.7 | 10.4 |
| 71 | CH | OCH₃ | OCH₃ | 3-CH₃C₆H₄ | CO₂CH₃ | 122.8 | 60.4 | 5.7 | 8.8 |
| | | | | | | | 59.7 | 5.7 | 9.4 |
| 72 | CH | OCH₃ | OCH₃ | 4-CH₃C₆H₄ | COCH₃ | 113.8 | 60.4 | 5.7 | 8.8 |
| | | | | | | | 60.7 | 6.0 | 8.9 |
| 73 | CH | OCH₃ | N(CH₃)₂ | C₆H₅ | CO₂CH₃ | 94.1 | 60.6 | 6.0 | 13.2 |
| | | | | | | | 60.6 | 5.9 | 13.3 |
| 74 | CH | OCH₃ | OCH₃ | 2,6-diClC₆H₃ | COOH | 246.6 | 46.8 | 3.4 | 7.8 |
| | | | | | | | 47.1 | 3.4 | 8.0 |
| 75 | N | OCH₃ | OCH₃ | C₆H₅ | CO₂CH₃ (R) | 95.0 | 55.1 | 5.0 | 13.8 |
| | | | | | | | 55.7 | 5.0 | 13.7 |
| 76 | N | OCH₃ | OCH₃ | C₆H₅ | CO₂CH₃ (S) | 98.0 | 55.1 | 5.0 | 13.8 |
| | | | | | | | 55.1 | 5.0 | 14.4 |
| 77 | N | OCH₃ | OCH₃ | 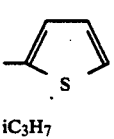 | CO₂CH₃ | 67.3 | 46.3 | 4.2 | 13.5 |
| | | | | | | | 46.4 | 4.1 | 13.2 |
| 78 | CH | OCH₃ | OCH₃ | iC₃H₇ | COO⁻NA⁺ | 196.1 | 47.5 | 5.4 | 10.1 |
| | | | | | | | 46.5 | 5.4 | 9.9 |

TABLE 1-continued

| Example | A | $R^1$ | $R^2$ | $R^3$ | $R^4$ | Melting Point (°C.) | Analysis (%) Calc / Found C | H | N |
|---|---|---|---|---|---|---|---|---|---|
| 79 | CH | $OCH_3$ | $OCH_3$ | $iC_3H_7$ | $CO_2CH_3$ (S) | 41.0 | 53.3 / 54.2 | 5.7 / 6.6 | 10.4 / 10.5 |
| 80 | CH | $OCH_3$ | $OCH_3$ | $iC_3H_7$ | $CO_2CH_3$ | 47.0 | 53.3 / 53.4 | 6.7 / 7.1 | 10.4 / 9.9 |
| 81 | CH | $OCH_3$ | $OCH_3$ | $iC_3H_7$ | $CO_2C_2H_5$ | 45.5–46.0 | 54.9 / 53.5 | 7.0 / 6.9 | 9.9 / 9.7 |
| 82 | CH | $OCH_3$ | $OCH_3$ | $iC_3H_7$ | $CO_2iC_3H_7$ | 46.0–46.5 | 56.4 / 56.3 | 7.0 / 7.2 | 9.9 / 9.7 |
| 83 | CH | $OCH_3$ | $OCH_3$ | $iC_3H_7$ | $CO_2nC_4H_9$ | 41.5–42.0 | 57.7 / 56.9 | 7.7 / 7.2 | 9.0 / 8.7 |
| 84 | CH | $OCH_3$ | $OCH_3$ | $nC_6H_{13}$ | COOH | 105.6 | 56.4 / 56.8 | 7.4 / 7.6 | 9.4 / 8.7 |
| 85 | CH | $OCH_3$ | $OCH_3$ | cyclohexyl | COOH (R) | 162.5 | 56.7 / 55.6 | 6.8 / 6.7 | 9.5 / 9.4 |
| 86 | CH | $OCH_3$ | $OCH_3$ | cyclohexyl | COOH (S) | 152.0 | 56.7 / 55.7 | 6.8 / 6.8 | 9.5 / 8.9 |
| 87 | CH | $OCH_3$ | $OCH_3$ | $(CH_2)_2SCH_3$ | COOH | 85.6 | 45.8 / 44.5 | 5.6 / 5.5 | 9.7 / 9.5 |
| 88 | CH | $OCH_3$ | $OCH_3$ | $COCO_2CH_3$ | $CO_2CH_3$ | 98.0 | 45.9 / 43.5 | 4.5 / 5.0 | 8.9 / 8.1 |
| 89 | CH | $OCH_3$ | $OCH_3$ | $CON(CH_3)_2$ | $CO_2CH_3$ | 133.0–134.0 | 48.2 / 47.9 | 5.7 / 5.7 | 14.0 / 13.5 |
| 90 | CH | $OCH_3$ | $OCH_3$ | $iC_3H_7$ | $CO_2(CH_2)_2OC_2H_5$ | 46.4 | 54.9 / 55.1 | 7.3 / 8.2 | 8.5 / 8.4 |
| 91 | CH | $OCH_3$ | $OCH_3$ | $iC_3H_7$ | $CO_2N=C(CH_3)_2$ | oil | 54.0 / 54.3 | 6.8 / 6.8 | 13.5 / 13.5 |
| 92 | CH | $OCH_3$ | $OCH_3$ | $iC_3H_7$ | $CO_2CH_2$-(2-thienyl) | 115.2 | 54.5 / 54.1 | 5.7 / 5.9 | 8.0 / 7.7 |
| 93 | CH | $OCH_3$ | $OCH_3$ | $iC_3H_7$ | $CO_2CH_2C_6H_5$ | 78.0 | 62.4 / 62.3 | 6.4 / 6.5 | 8.1 / 8.4 |
| 94 | CH | $OCH_3$ | $OCH_3$ | $iC_3H_7$ | $CO_2CH_2C{\equiv}CH$ | 75.7 | 57.1 / 57.4 | 6.1 / 6.8 | 9.5 / 9.9 |
| 95 | CH | $OCH_3$ | $OCH_3$ | $iC_3H_7$ | $CO_2$-(3-methylphenyl) | 80.6 | 62.4 / 62.2 | 6.4 / 6.9 | 8.1 / 8.4 |
| 96 | CH | $OCH_3$ | $OCH_3$ | $iC_3H_7$ | $CO_2iC_4H_9$ | 43.0 | 57.7 / 57.8 | 7.7 / 8.1 | 8.9 / 9.3 |
| 97 | CH | $OCH_3$ | $OCH_3$ | $iC_3H_7$ | $COSnC_3H_7$ | 52.2 | 53.5 / 53.8 | 7.0 / 7.2 | 8.9 / 9.1 |
| 98 | CH | $OCH_3$ | $OCH_3$ | $iC_3H_7$ | $COSC_6H_5$ | 130.7 | 58.6 / 58.5 | 5.7 / 5.9 | 8.0 / 8.3 |
| 99 | CH | $OCH_3$ | $OCH_3$ | $iC_3H_7$ | $CO_2sC_4H_9$ | 43.1 | 57.7 / 57.5 | 7.7 / 7.5 | 8.9 / 8.9 |
| 100 | CH | $OCH_3$ | $OCH_3$ | $iC_3H_7$ | $CO_2CH(CH_3)C_6H_5$ | oil | 63.3 / 63.3 | 6.7 / 6.5 | 7.8 / 8.0 |
| 101 | CH | $OCH_3$ | $OCH_3$ | $iC_3H_7$ | $CO_2(CH_2)_2SCH_3$ | 47.9 | 50.9 / 51.1 | 6.7 / 6.4 | 8.5 / 8.6 |
| 102 | CH | $OCH_3$ | $OCH_3$ | $iC_3H_7$ | $CO_2(CH_2)_2Cl$ | 38.5 | 48.9 / 49.3 | 6.0 / 6.1 | 9.3 / 8.8 |
| 103 | CH | $OCH_3$ | $OCH_3$ | $iC_3H_7$ | $CO_2CH_2$-(2-furyl) | 110.6 | 57.1 / 56.8 | 5.9 / 6.2 | 8.3 / 9.0 |
| 104 | CH | $OCH_3$ | $OCH_3$ | $iC_3H_7$ | $CO_2CH_2$-(tetrahydro-2-furyl) | oil | 56.5 / 56.8 | 7.1 / 7.1 | 8.2 / 8.5 |
| 105 | CH | $OCH_3$ | $OCH_3$ | $iC_3H_7$ | $CO_2CH_2$-(2,4-dichlorophenyl) | 110.4 | 52.0 / 52.1 | 4.8 / 5.0 | 6.7 / 6.4 |

TABLE 1-continued

| Example | A | $R^1$ | $R^2$ | $R^3$ | $R^4$ | Melting Point (°C.) | Analysis (%) Calc / Found C | H | N |
|---|---|---|---|---|---|---|---|---|---|
| 106 | CH | $OCH_3$ | $OCH_3$ | $iC_3H_7$ | $CO_2CH_2$-(4-Cl-C$_6$H$_4$) | 92.9 | 56.8 / 56.5 | 5.5 / 5.6 | 7.4 / 6.9 |
| 107 | CH | $OCH_3$ | $OCH_3$ | $iC_3H_7$ | $CO_2CH_2$-(4-OCH$_3$-C$_6$H$_4$) | oil | 60.6 / 60.0 | 6.4 / 5.9 | 7.4 / 7.3 |
| 108 | CH | $OCH_3$ | $OCH_3$ | $iC_3H_7$ | $CONHN(CH_3)_2$ | 130.8 | 52.3 / 52.2 | 7.4 / 7.9 | 18.8 / 18.9 |
| 109 | CH | $OCH_3$ | $OCH_3$ | $iC_3H_7$ | $CO_2CH_2$-(3-OCH$_3$-C$_6$H$_4$) | 49.0 | 60.6 / 60.0 | 6.4 / 5.9 | 7.4 / 7.3 |
| 110 | CH | $OCH_3$ | $OCH_3$ | $iC_3H_7$ | $CONHNH_2$ | 178.1 | 48.9 / 49.1 | 6.7 / 6.8 | 20.7 / 19.9 |
| 111 | CH | $OCH_3$ | $OCH_3$ | $iC_3H_7$ | $CONH$-(2-CO$_2$CH$_3$-C$_6$H$_4$) | 98.0 | 58.6 / 58.1 | 5.9 / 6.0 | 10.8 / 10.5 |
| 112 | CH | $OCH_3$ | $OCH_3$ | $iC_3H_7$ | $CO_2$-(4-NO$_2$-C$_6$H$_4$) | 172.6 | 54.1 / 54.6 | 5.0 / 5.3 | 11.1 / 11.1 |
| 113 | CH | $OCH_3$ | $OCH_3$ | $iC_3H_7$ | $CO_2$-(3-CH$_2$OH-C$_6$H$_4$) | oil | 59.7 / 60.3 | 6.1 / 6.5 | 7.7 / 7.0 |
| 114 | CH | $OCH_3$ | $OCH_3$ | $iC_3H_7$ | (complex ester structure, see image) | 130.3 | 58.0 / 57.4 | 6.0 / 5.8 | 9.3 / 8.8 |
| 115 | CH | $OCH_3$ | $OCH$ | $tC_4H_9$ | $CO_2CH_2C\equiv CH$ | 95.0 | 58.5 / 58.4 | 6.5 / 6.5 | 9.1 / 9.0 |
| 116 | CH | $OCH_3$ | $OCH_3$ | $tC_4H_9$ | $COSnC_3H_7$ | 76.0 | 54.9 / 55.7 | 7.3 / 7.4 | 8.5 / 8.8 |
| 117 | CH | $OCH_3$ | $OCH_3$ | $tC_4H_9$ | $CO_2N=C(CH_3)_2$ | oil | 55.4 | 7.1 | 12.9 |
| 118 | CH | $CH_3$ | $CH_3$ | $nC_3H_7$ | COOH | 79.6 | 60.6 / 59.2 | 7.3 / 7.0 | 12.8 / 12.8 |
| 119 | CH | $CH_3$ | $CH_3$ | $nC_4H_9$ | COOH | 65.2 | 60.5 / 60.5 | 7.5 / 7.4 | 11.8 / 11.8 |
| 120 | CH | $CH_3$ | $CH_3$ | $tC_4H_9$ | COOH | 168.0–168.5 | 60.5 / 59.9 | 7.5 / 7.3 | 11.8 / 11.4 |
| 121 | CH | $CH_3$ | $CH_3$ | $CH_2C_6H_5$ | $CO_2CH_3$ | 71.0–72.5 | 67.1 / 67.4 | 6.3 / 6.3 | 9.8 / 10.0 |
| 122 | CH | $CH_3$ | $CH_3$ | $CO_2C_2H_5$ | $CO_2C_2H_5$ | oil | 55.3 / 55.4 | 6.4 / 6.5 | 9.9 / 9.7 |
| 123 | CH | $CH_3$ | $CH_3$ | COOH (Dihydrate) | COOH | 231.2 | 41.2 / 40.2 | 5.3 / 4.9 | 10.7 / 10.8 |
| 124 | CH | $CH_3$ | $CH_3$ | $CH_2C_6H_5$ | COOH | 206.0 | 66.2 | 5.9 | 10.3 |

TABLE 1-continued

| Example | A | R¹ | R² | R³ | R⁴ | Melting Point (°C.) | Analysis (%) Calc Found | | |
|---|---|---|---|---|---|---|---|---|---|
| | | | | | | | C | H | N |
| 125 | CH | CH₃ | CH₃ | nC₄H₉ | CO₂C₂H₅ | oil | 65.5<br>63.1<br>63.6 | 5.9<br>8.3<br>8.2 | 10.3<br>10.5<br>10.0 |
| 126 | CH | CH₃ | CH₃ | nC₃H₇ | CO₂C₂H₅ | oil | 61.9<br>62.2 | 8.0<br>8.0 | 11.1<br>10.4 |
| 127 | CH | OCH₃ | Cl | iC₃H₇ | CO₂CH₃ | oil | 48.1<br>48.0 | 5.5<br>5.4 | 10.2<br>10.0 |
| 128 | CH | OCH₃ | SCH₃ | iC₃H₇ | CO₂CH₃ | oil | 50.3<br>49.9 | 6.3<br>6.3 | 9.8<br>9.6 |
| 129 | CH | OCH₃ | N(CH₃)₂ | iC₃H₇ | CO₂CH₃ | oil | 55.1<br>55.9 | 7.4<br>7.9 | 14.8<br>13.8 |
| 130 | CH | OCH₃ | NHCH₃ | iC₃H₇ | CO₂CH₃ | 100.5 | 53.5<br>54.1 | 7.1<br>7.4 | 15.6<br>15.7 |
| 131 | CH | OCH₃ | CH₃ | iC₃H₇ | CO₂CH₃ | oil | 56.7<br>56.9 | 7.1<br>7.5 | 11.0<br>10.9 |
| 132 | CH | OCH₃ | Cl | CH₂C₆H₅ | CO₂CH₃ | oil | 55.8<br>N/A | 4.7<br>N/A | 8.7<br>N/A |
| 133 | CH | OCH₃ | Cl | CH₂C₆H₅ | CO₂C₂H₅ | oil | 57.1<br>57.3 | 5.1<br>5.2 | 8.3<br>8.4 |
| 134 | CH | OCH₃ | SCH₃ | CH₂C₆H₅ | CO₂CH₃ | oil | 57.5<br>57.2 | 5.4<br>5.4 | 8.4<br>8.4 |
| 135 | CH | OCH₃ | N(CH₃)₂ | CH₂C₆H₅ | CO₂CH₃ | 90.0 | 61.6<br>62.2 | 6.3<br>6.4 | 12.7<br>12.9 |
| 136 | CH | OCH₃ | NHCH₃ | CH₂C₆H₅ | CO₂CH₃ | 80.0 | 60.6<br>61.0 | 6.0<br>6.0 | 13.3<br>13.2 |
| 137 | CH | OCH₃ | CH₃ | CH₂C₆H₅ | CO₂CH₃ | oil | 63.6<br>63.4 | 6.0<br>6.2 | 9.3<br>9.4 |
| 138 | CH | OCH₃ | OC₂H₅ | CH₂C₆H₅ | CO₂C₂H₅ | oil | 62.4<br>62.7 | 6.4<br>6.7 | 8.1<br>8.4 |
| 139 | CH | OC₂H₅ | Cl | CH₂C₆H₅ | CO₂C₂H₅ | oil | 58.2<br>N/A | 5.4<br>N/A | 8.0<br>N/A |
| 140 | CH | OCH₃ | Cl | iC₄H₉ | CO₂CH₃ | oil | 49.9<br>49.8 | 5.9<br>5.8 | 9.7<br>9.5 |
| 141 | CH | OCH₃ | Cl | iC₄H₉ | COOH | 84.8 | 48.1<br>47.8 | 5.5<br>5.5 | 10.2<br>10.6 |
| 142 | CH | OCH₃ | Cl | nC₄H₉ | CO₂C₂H₅ | oil | 51.6<br>51.9 | 6.3<br>6.3 | 9.3<br>9.2 |
| 143 | CH | OCH₃ | Cl | nC₄H₉ | COOH | 100.4 | 48.1<br>48.5 | 5.5<br>5.5 | 10.2<br>10.3 |
| 144 | CH | OCH₃ | Cl | iC₃H₇ | COOH | 133.3 | 46.1<br>46.5 | 5.0<br>5.1 | 10.8<br>10.7 |
| 145 | CH | OCH₃ | Cl | tC₄H₉ | CO₂CH₃ | 66.1 | 49.9<br>50.3 | 5.9<br>6.0 | 9.7<br>9.9 |
| 146 | N | OCH₃ | Cl | iC₃H₇ | CO₂CH₃ | oil | 43.6<br>43.8 | 5.1<br>5.0 | 15.2<br>15.0 |
| 147 | N | OCH₃ | SCH₃ | iC₃H₇ | CO₂CH₃ | oil | 46.0<br>46.3 | 5.9<br>6.0 | 14.6<br>14.3 |
| 148 | CH | OCH₃ | N(CH₃)₂ | iC₃H₇ | CO₂CH₃ | oil | 50.7<br>51.5 | 7.0<br>7.1 | 19.7<br>19.5 |
| 149 | N | OCH₃ | NHCH₃ | iC₃H₇ | CO₂CH₃ | 91.5 | 48.9<br>48.9 | 6.7<br>6.6 | 20.7<br>21.0 |
| 150 | N | OCH₃ | CH₃ | iC₃H₇ | CO₂CH₃ | oil | 51.8<br>52.3 | 6.7<br>6.7 | 16.5<br>15.9 |
| 151 | N | OCH₃ | OCH₃ | nC₄H₉ | CO₂CH₃ | oil | 50.5<br>51.7 | 6.7<br>6.8 | 14.7<br>12.3 |
| 152 | N | OCH₃ | OCH₃ | sC₄H₉ | CO₂CH₃ | oil | 50.5<br>50.4 | 6.7<br>6.7 | 14.7<br>12.0 |
| 153 | N | OCH₃ | OCH₃ | tC₄H₉ | CO₂CH₃ | 68.0 | 50.5<br>50.4 | 6.7<br>6.8 | 14.7<br>14.9 |
| 154 | N | OCH₃ | CH₃ | CH₂C₆H₅ | CO₂CH₃ | oil | 59.4<br>59.5 | 5.6<br>5.7 | 13.9<br>13.4 |
| 155 | N | OCH₃ | OCH₃ | iC₃H₇ | CO₂CH₂C₆H₅ | 84.9 | 58.8<br>58.0 | 6.1<br>6.4 | 12.1<br>12.1 |
| 156 | N | OCH₃ | OCH₃ | nC₄H₉ | CO₂CH₂C₆H₅ | 59.5 | 59.8<br>59.6 | 6.4<br>6.6 | 11.6<br>11.8 |
| 157 | N | OCH₃ | OCH₃ | iC₄H₉ | CO₂CH₂C₆H₅ | 60.2 | 59.9<br>59.4 | 6.4<br>6.7 | 11.6<br>11.7 |
| 158 | N | OCH₃ | OCH₃ | tC₄H₉ | CO₂CH₂C₆H₅ | 76.5 | 59.7<br>59.3 | 6.6<br>6.4 | 11.6<br>12.1 |
| 159 | N | OCH₃ | OCH₃ | iC₃H₇ | COOH | 115.8 | 46.7<br>46.5 | 5.8<br>5.9 | 16.3<br>16.4 |
| 160 | N | OCH₃ | OCH₃ | nC₄H₉ | COOH | 82.9 | 48.7<br>48.4 | 6.3<br>6.2 | 15.5<br>14.9 |
| 161 | N | OCH₃ | OCH₃ | iC₄H₉ | COOH | 90.7 | 48.7<br>48.5 | 6.3<br>6.2 | 15.5<br>15.4 |
| 162 | N | OCH₃ | OCH₃ | tC₄H₉ | COOH | 131.6 | 48.7<br>49.2 | 6.3<br>6.3 | 15.5<br>15.3 |
| 163 | N | OCH₃ | N(CH₃)₂ | iC₃H₇ | CO₂CH₂C₆H₅ | | 60.0 | 6.7 | 15.6 |

TABLE 1-continued

| Example | A | $R^1$ | $R^2$ | $R^3$ | $R^4$ | Melting Point (°C.) | Analysis (%) Calc Found C | H | N |
|---|---|---|---|---|---|---|---|---|---|
| | | | | | | | 60.0 | 6.7 | 15.5 |

EXAMPLE 164

Methyl 2-(4,6-dimethoxypyrimidin-2-yl)oxybut-2-enoate

A mixture of methyl 2-hydroxybut-3-enoate (0.80g, 6.9mmol), 4,6-dimethoxy-2-methanesulphonylpyrimidine (1.50g, 6.9mmol) and potassium carbonate (1.04g, 7.6mmol) in methyl ethyl ketone (100ml) was refluxed for 12 hours. The reaction mixture was filtered and the filtrate evaporated in vacuo. Flash column chromatography (silica, 1.5% methanol in chloroform) of the residue gave the title compound (1.37g, 78% yield by weight).

Melting point: 71.0° C.

Analysis (%) : Calc. C 52.0. H 5.5. N 11.0. Found C 50.6. H 5.8. N 10.5.

Examination of the product by nmr spectroscopic analysis confirms the structure as methyl 2-(4,6-dimethoxypyrimidin-2-yl)oxybut-2-enoate.

EXAMPLES 165 TO 168

By methods analogous to those described in Example 164, further compounds of the general formula

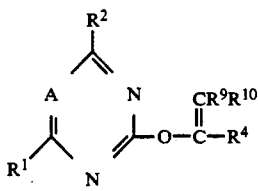

were prepared. Details are given in Table IA.

TABLE IA

| Example | A | $R^1$ | $R^2$ | $R^4$ | $R^9$ | $R^{10}$ | Melting Point (°C.) | Analysis (%) Calc Found C | H | N |
|---|---|---|---|---|---|---|---|---|---|---|
| 165 | CH | $CH_3$ | $CH_3$ | $CO_2CH_3$ | H | $CH_3$ | oil (boiling point 100–110° C. at 2.0 mm Hg) | 59.5 58.2 | 6.3 6.4 | 12.6 12.5 |
| 166 | CH | $CH_3$ | $CH_3$ | COOH | H | $CH_3$ | N/A | 57.7 57.4 | 5.8 5.9 | 13.5 12.8 |
| 167 | CH | $OCH_3$ | $CH_3$ | COOH | H | $CH_3$ | 122.0 | 50.0 50.2 | 5.0 5.3 | 11.7 11.3 |
| 168 | N | $OCH_3$ | $OCH_3$ | $CO_2CH_3$ | H | $CH_3$ | oil | 47.1 48.3 | 5.1 5.5 | 16.5 16.3 |

EXAMPLE 169

Herbicidal Activity

To evaluate their herbicidal activity, compounds according to the invention were tested using as representative range of plants: maize, Zea mays (Mz); rice, Oryza sativa (R); barnyard grass, Echinochloa crusqalli (BG); oat, Avena sativa (O); linseed, Linum usitatissimum (L); mustard, Sinapsis alba (M); sugar beet, Beta vulgaris (SB) and soya bean, Glycine max (S).

The tests fall into two categories, pre-emergence and post-emergence. The pre-emergence tests involved spraying a liquid formulation of the compound onto the soil in which the seeds of the plant specied mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 litres per hectare in the soil spray and foliar spray test, and at a dosage of level equivalent to 10 kilograms of active material per hectare in a volume equivalent to approximately 3,000 litres per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table II below, in which the compounds are identified by reference to the preceding examples. Absence of a numeral in the Table indicates a zero rating; an asterisk indicates that no result was obtained.

TABLE II

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 1 | | 7 | 8 | 7 | 5 | 7 | 3 | | 5 | | 3 | 8 | 5 | | 8 | 4 | 3 | | 8 | 8 | 7 | | 8 | 4 | |
| | | | | | | | | | 1 | | | 6 | 3 | | 7 | 2 | | | 5 | 5 | 4 | | 3 | 2 | |
| 2 | 3 | 8 | 8 | 7 | 4 | 8 | 7 | | 5 | | 6 | 8 | 6 | 4 | 8 | 5 | 2 | | 9 | 8 | 7 | 4 | 8 | 6 | |
| | | | | | | | | | 1 | | 5 | 8 | 5 | | 7 | 1 | | | 8 | 8 | 6 | | 7 | 2 | |
| 3 | 8 | 7 | 8 | 7 | 7 | 9 | 9 | 8 | 5 | 5 | 5 | 8 | 5 | 8 | 9 | 9 | 8 | 8 | 8 | 8 | 7 | 8 | 8 | 8 | 8 |
| | | | | | | | | | 1 | | 1 | 8 | 2 | 7 | 9 | 8 | 7 | 5 | 6 | 8 | 4 | 4 | 8 | 8 | 7 |
| 4 | 7 | 6 | 8 | 5 | 8 | 8 | 9 | 7 | 5 | 7 | 5 | 8 | 5 | 8 | 9 | 9 | 7 | 6 | 8 | 8 | 5 | 6 | 8 | 8 | 7 |
| | | | | | | | | | 1 | 2 | 2 | 7 | 1 | | 8 | 8 | 7 | | 4 | 6 | | | 5 | 7 | 4 |
| 5 | 7 | 7 | 8 | 7 | 6 | 7 | 5 | 4 | 5 | 7 | 7 | 8 | 7 | 7 | 8 | 5 | 5 | 9 | 9 | 8 | 7 | 7 | 8 | 4 | 4 |
| | | | | | | | | | 1 | 6 | 5 | 8 | 6 | 7 | 8 | 5 | 3 | 8 | 9 | 8 | 5 | 4 | 6 | 1 | |
| 6 | 7 | 7 | 6 | 7 | 1 | 5 | 4 | | 5 | 6 | 5 | 7 | 7 | 5 | 7 | 6 | 4 | 5 | 8 | 7 | 6 | 2 | 5 | 2 | |
| | | | | | | | | | 1 | 5 | 5 | 7 | 6 | 3 | 7 | 5 | 1 | 3 | 6 | 5 | 4 | 1 | | | |
| 7 | | | | | | | 3 | | 5 | | | | | | | 5 | | | | | | | | | |
| | | | | | | | | | 1 | | | | | | | 4 | | | | | | | | | |
| 8 | | | | | | | 4 | | 5 | | | | | | 3 | 2 | | | | | | | | | |
| | | | | | | | | | 1 | | | | | | | | | | | | | | | | |
| 9 | 8 | 8 | 7 | 8 | 2 | 8 | 8 | 2 | 5 | 8 | 7 | 8 | 8 | | 9 | 9 | 4 | 7 | 9 | 8 | 8 | | 8 | 8 | 2 |
| | | | | | | | | | 1 | 6 | 7 | 7 | 8 | | 8 | 8 | 3 | 3 | 8 | 7 | 8 | | 7 | 8 | |
| 10 | 7 | 7 | 7 | 6 | 6 | 8 | 9 | 3 | 5 | 7 | 6 | 8 | 6 | 2 | 8 | 9 | 6 | 8 | 9 | 8 | 7 | 7 | 7 | 8 | 2 |
| | | | | | | | | | 1 | 7 | 5 | 7 | 5 | | 8 | 8 | 5 | 7 | 9 | 8 | 7 | 7 | 7 | 7 | |
| 11 | 7 | 7 | 6 | 7 | 3 | 7 | 7 | | 5 | 6 | 7 | 8 | 7 | 5 | 8 | 6 | 5 | 7 | 8 | 8 | 7 | 4 | 5 | 5 | 2 |
| | | | | | | | | | 1 | 1 | 4 | 6 | 4 | 2 | 6 | 3 | | 5 | 6 | 5 | 4 | | 2 | 2 | |
| 12 | 7 | 6 | 7 | 6 | | | 3 | 5 | 5 | 7 | 6 | 7 | 7 | 6 | 8 | 8 | 4 | 6 | 7 | 8 | 7 | 2 | 4 | 4 | |
| | | | | | | | | | 1 | 3 | 5 | 6 | 7 | 4 | 7 | 4 | 1 | 2 | 4 | 5 | 3 | | 1 | | |
| 13 | | | | | | | 6 | | 5 | | 1 | | | | 4 | 8 | 2 | | 2 | | | | | 7 | |
| | | | | | | | | | 1 | | | | | | 1 | 7 | | | 1 | | | | | 4 | |
| 14 | | | | | | | | | 5 | | | | | | 3 | 4 | | | | | | | | | |
| | | | | | | | | | 1 | | | | | | 1 | 1 | | | | | | | | | |
| 15 | 3 | 4 | 5 | | 4 | 3 | 6 | 3 | 5 | | | 6 | 4 | 6 | 5 | 8 | 4 | | | | | | | | |
| | | | | | | | | | 1 | | | 6 | | 4 | 4 | 6 | 3 | | | | | | | | |
| 18 | | | | | | | | | 5 | | | | | | 5 | 5 | | | | | * | | | | |
| | | | | | | | | | 1 | | | | | | | 2 | | | | | | | | | |
| 19 | | | | | | | | | 5 | | | | | | 7 | 7 | 2 | | | | | | | | |
| | | | | | | | | | 1 | | | | | | 5 | 5 | | | | | | | | | |
| 20 | 7 | 8 | 8 | 7 | 5 | 5 | 7 | 4 | 5 | 7 | 8 | 8 | 7 | 7 | 7 | 8 | 8 | 7 | 9 | 8 | 6 | 6 | 5 | 8 | 5 |
| | | | | | | | | | 1 | 7 | 7 | 8 | 7 | 5 | 7 | 8 | 7 | 4 | 7 | 8 | 5 | 4 | 4 | 6 | 4 |
| 21 | 6 | 6 | 6 | 7 | 2 | 4 | 4 | | 5 | 4 | 7 | 8 | 7 | 3 | 6 | 7 | 4 | 4 | 6 | 4 | 3 | 2 | 4 | | 2 |
| | | | | | | | | | 1 | 3 | 3 | 7 | 7 | | 5 | 4 | 2 | 3 | 2 | | | | 2 | | |
| 22 | 8 | 7 | 8 | 7 | 7 | 8 | 9 | 3 | 5 | 7 | 7 | 8 | 7 | 7 | 8 | 8 | 8 | 8 | 9 | 8 | 7 | 7 | 7 | 8 | 8 |
| | | | | | | | | | 1 | 6 | 6 | 7 | 7 | 7 | 7 | 7 | 6 | 6 | 7 | 6 | 5 | 6 | 6 | 6 | 8 |
| 24 | 7 | 4 | | 6 | 5 | 3 | 2 | | 5 | 7 | 7 | 7 | 7 | 7 | 8 | 7 | 5 | 5 | 7 | 7 | 7 | 6 | 4 | 5 | 2 |
| | | | | | | | | | 1 | 6 | 5 | 2 | 7 | 7 | 4 | 6 | 2 | 2 | 2 | 2 | 4 | 4 | 3 | | 1 |
| 25 | | | | 2 | | | 2 | | 5 | | | | 3 | 2 | 7 | 5 | | | 4 | 2 | 3 | 3 | | | |
| | | | | | | | | | 1 | | | | | 1 | 3 | 2 | | | | | 2 | | | | |
| 26 | | | | | 2 | 4 | | | 5 | 2 | | | 3 | | 7 | 8 | 3 | | 3 | 2 | 3 | | | 3 | |
| | | | | | | | | | 1 | | | | 2 | | 4 | 6 | 2 | | | | 2 | | | | |
| 27 | 8 | 6 | 8 | 8 | 7 | 8 | 8 | 7 | 5 | 8 | 7 | 8 | 8 | 8 | 9 | 8 | 7 | 7 | * | 8 | 7 | 5 | 7 | 8 | 3 |
| | | | | | | | | | 1 | 6 | 6 | 8 | 7 | 7 | 9 | 7 | 7 | 4 | * | 8 | 4 | 3 | 7 | 5 | 1 |
| 28 | 7 | 6 | 7 | 5 | 2 | 7 | 8 | 4 | 5 | 2 | | 7 | 2 | | 4 | 7 | 5 | 2 | 3 | 4 | | 2 | | * | |
| | | | | | | | | | 1 | | 6 | | | | 2 | 2 | | | | 3 | | | | | |
| 29 | 6 | 4 | 8 | 3 | 3 | 7 | 8 | 4 | 5 | 2 | | 8 | 2 | 7 | 8 | 8 | 7 | 5 | 6 | 8 | * | 4 | 7 | 7 | 3 |
| | | | | | | | | | 1 | 1 | | 8 | 1 | 5 | 8 | 8 | 6 | 3 | 3 | 8 | | 1 | 6 | 5 | |
| 30 | 7 | 4 | 8 | 5 | 2 | 8 | 7 | 5 | 5 | 5 | 5 | 7 | 5 | 4 | 9 | 8 | 7 | 4 | * | 8 | 3 | | 7 | 8 | 4 |
| | | | | | | | | | 1 | 2 | 3 | 7 | 2 | 1 | 8 | 7 | 6 | 1 | 4 | 7 | | | 6 | 7 | 1 |
| 31 | * | * | * | * | * | * | * | * | 5 | 3 | 4 | 7 | 4 | 5 | 6 | 7 | 4 | 6 | 6 | 7 | 4 | 6 | 7 | 7 | 3 |
| | | | | | | | | | 1 | 1 | 1 | 6 | 2 | 4 | 5 | 6 | 4 | 2 | | 6 | 1 | 2 | 5 | 5 | |
| 32 | 7 | 7 | 7 | 6 | 5 | 8 | 7 | 5 | 5 | 7 | 6 | 6 | 4 | 3 | 8 | 9 | 6 | 7 | 8 | 9 | 6 | 7 | 7 | 8 | 8 |
| | | | | | | | | | 1 | 3 | 4 | 6 | 3 | 1 | 8 | 7 | 5 | 5 | 6 | 8 | 4 | 3 | 7 | 7 | 7 |
| 33 | 6 | 6 | 6 | 4 | 6 | 5 | 6 | 3 | 5 | | 3 | 6 | 2 | 6 | 7 | 8 | 5 | 4 | 5 | 7 | 3 | 4 | 5 | 7 | 2 |
| | | | | | | | | | 1 | | 2 | 5 | 1 | 5 | 6 | 6 | 3 | 3 | 3 | 6 | 1 | 3 | 3 | 6 | |
| 34 | 7 | 7 | 7 | 6 | 4 | 8 | 8 | 4 | 5 | 5 | 6 | 6 | 5 | 4 | 8 | 8 | 6 | 6 | 7 | 8 | 3 | 4 | 7 | 7 | 7 |
| | | | | | | | | | 1 | 4 | 2 | 5 | 3 | 2 | 8 | 8 | 5 | 6 | 6 | 8 | 1 | 2 | 7 | 7 | 6 |
| 35 | 7 | 4 | 7 | 7 | 6 | 8 | 8 | 4 | 5 | 6 | 6 | 7 | 7 | 5 | 8 | 9 | 6 | 8 | 9 | 8 | 7 | 3 | 6 | 8 | 4 |
| | | | | | | | | | 1 | 6 | 5 | 7 | 7 | | 8 | 7 | 5 | 4 | 9 | 7 | 7 | | 5 | 6 | 2 |
| 36 | 3 | 3 | 2 | | | 2 | 3 | | 5 | 2 | 4 | 6 | 4 | 3 | 7 | 5 | 4 | | 5 | 4 | | | | | |
| | | | | | | | | | 1 | | 1 | | 3 | | 1 | 2 | | | 2 | | | | | | |
| 37 | 7 | 7 | 8 | 7 | 7 | 9 | 8 | 6 | 5 | 5 | 5 | 8 | 6 | 7 | 8 | 8 | 7 | 7 | 8 | 8 | 7 | 7 | 7 | 7 | 7 |
| | | | | | | | | | 1 | 1 | | 7 | 2 | 5 | 6 | 7 | 4 | 5 | 6 | 7 | 4 | 3 | 7 | 7 | 2 |
| 38 | 5 | 5 | 6 | 5 | | 7 | 7 | | 5 | 3 | 4 | 8 | 7 | 3 | 7 | 7 | 3 | 5 | 9 | 7 | 5 | 3 | 3 | 3 | |
| | | | | | | | | | 1 | | | 2 | | 3 | 5 | 5 | 1 | 2 | 7 | 4 | 2 | 1 | 1 | | |
| 39 | | | | | | | 4 | | 5 | | | | | | 2 | 4 | | | | | | | | | |
| | | | | | | | | | 1 | | | | | | | 1 | | | | | | | | | |
| 40 | 4 | 5 | 6 | 4 | 2 | 3 | | | 5 | 4 | 6 | 7 | 7 | 3 | 8 | 5 | 5 | 4 | 7 | 6 | 4 | | 5 | 4 | 2 |
| | | | | | | | | | 1 | 1 | 3 | 4 | 5 | 1 | 6 | 2 | 1 | 1 | 2 | 2 | 1 | | 5 | 3 | |
| 42 | | | | | | | | | 5 | | | | | | 7 | | | | | | 2 | | | | |
| | | | | | | | | | 1 | | | | | | 3 | | | | | | 1 | | | | |
| 43 | | 6 | 7 | 7 | 1 | 7 | 1 | | 5 | | 5 | 8 | 7 | 1 | 8 | 3 | 3 | | 7 | 7 | 6 | | 6 | | |
| | | | | | | | | | 1 | | 1 | 4 | 3 | | 7 | 1 | | | 1 | 2 | 2 | | 3 | | |

TABLE II-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 44 | | 7 | 7 | 7 | | 8 | 1 | | 5 | | 7 | 8 | 7 | 1 | 8 | 4 | 3 | | 8 | 7 | 7 | | 7 | 2 | |
| | | | | | | | | | 1 | | 5 | 5 | 4 | | 7 | | | | 6 | 3 | 4 | | 4 | | |
| 45 | 7 | 7 | 8 | 7 | 7 | 8 | 9 | 7 | 5 | 7 | 7 | 8 | 7 | 4 | 8 | 8 | 7 | 8 | 9 | 8 | 8 | 7 | 7 | 8 | 4 |
| | | | | | | | | | 1 | 6 | 6 | 8 | 6 | 1 | 8 | 8 | 5 | 6 | 9 | 8 | 7 | 4 | 7 | 8 | |
| 46 | 8 | 7 | 8 | 7 | 7 | 8 | 9 | 7 | 5 | 7 | 7 | 8 | 7 | 3 | 8 | 8 | 7 | 8 | 9 | 9 | 7 | 7 | 7 | 8 | 4 |
| | | | | | | | | | 1 | 6 | 6 | 7 | 7 | 1 | 8 | 7 | 5 | 7 | 9 | 8 | 7 | 6 | 7 | 7 | |
| 47 | 5 | 6 | 8 | 7 | 6 | 8 | 8 | | 5 | 4 | 4 | 8 | 4 | 1 | 7 | 7 | 3 | 4 | 8 | 8 | 6 | | 7 | 6 | 2 |
| | | | | | | | | | 1 | 2 | 2 | 5 | 3 | | 5 | 4 | | | 7 | 7 | 2 | | 6 | 2 | |
| 48 | 7 | 7 | 8 | 7 | 6 | 8 | 8 | | 5 | 3 | 6 | 8 | 6 | | 7 | 5 | | 5 | 9 | 8 | 6 | 2 | 7 | 7 | |
| | | | | | | | | | 1 | 1 | 5 | 6 | 4 | | 7 | 2 | | 1 | 8 | 8 | 5 | | 7 | 4 | |
| 49 | 6 | 7 | 8 | 7 | 5 | 8 | 7 | 4 | 5 | 6 | 6 | 8 | 7 | 6 | 8 | 8 | 7 | 6 | 9 | 9 | 7 | 5 | 7 | 7 | 7 |
| | | | | | | | | | 1 | 3 | 2 | 7 | 7 | 4 | 8 | 6 | 5 | 2 | 9 | 8 | 7 | 2 | 7 | 4 | |
| 50 | 4 | 5 | 7 | 7 | 3 | 8 | 7 | 3 | 5 | | 2 | 8 | 7 | 3 | 8 | 5 | 4 | 3 | 8 | 8 | 7 | 2 | 7 | 4 | 2 |
| | | | | | | | | | 1 | | | 7 | 6 | | 7 | 4 | 1 | 1 | 7 | 4 | 4 | | 7 | 1 | |
| 51 | 7 | 7 | 8 | 7 | 5 | 8 | 8 | 2 | 5 | 6 | 6 | 8 | 7 | 4 | 8 | 8 | 7 | 6 | 9 | 9 | 7 | 5 | 7 | 8 | 2 |
| | | | | | | | | | 1 | 5 | 4 | 8 | 6 | | 8 | 7 | 5 | 2 | 9 | 9 | 7 | 2 | 7 | 7 | |
| 52 | 3 | 2 | 4 | 2 | 3 | 2 | 4 | | 5 | 4 | | 6 | 3 | 4 | 6 | 3 | 4 | | | | | | | | |
| | | | | | | | | | 1 | 1 | | 2 | | 1 | 3 | 1 | | | | | | | | | |
| 53 | 7 | 7 | 8 | 7 | 6 | 7 | 7 | 4 | 5 | 7 | 7 | 8 | 6 | 7 | 8 | 8 | 7 | 7 | 9 | 8 | 8 | 8 | 7 | 7 | 8 |
| | | | | | | | | | 1 | 5 | 5 | 8 | 4 | 6 | 7 | 5 | 5 | 5 | 8 | 8 | 7 | 4 | 6 | 6 | 8 |
| 54 | 8 | 8 | 9 | 8 | 8 | 9 | 9 | 7 | 5 | 7 | 7 | 8 | 8 | 7 | 9 | 8 | 8 | 9 | 9 | 9 | 8 | 9 | 7 | 8 | 8 |
| | | | | | | | | | 1 | 7 | 7 | 8 | 8 | 6 | 8 | 8 | 8 | 9 | 9 | 9 | 8 | 8 | 7 | 8 | 8 |
| 55 | 7 | 8 | 8 | 7 | 7 | 8 | 9 | 7 | 5 | 6 | 6 | 8 | 6 | 7 | 9 | 8 | 8 | 8 | 9 | 9 | 7 | 6 | 6 | 8 | 8 |
| | | | | | | | | | 1 | 5 | 4 | 7 | 6 | 5 | 7 | 8 | 7 | 6 | 8 | 8 | 6 | 4 | 6 | 8 | 5 |
| 56 | 7 | 7 | 8 | 7 | 7 | 8 | 8 | 8 | 5 | 7 | 5 | 8 | 7 | 7 | 8 | 8 | 8 | 9 | 9 | 9 | 8 | 9 | 7 | 8 | 8 |
| | | | | | | | | | 1 | 6 | 4 | 8 | 6 | 7 | 7 | 7 | 8 | 9 | 9 | 9 | 7 | 7 | 7 | 7 | 7 |
| 57 | 7 | 7 | 8 | 7 | 7 | 8 | 8 | 7 | 5 | 7 | 5 | 8 | 7 | 7 | 7 | 8 | 7 | 8 | 9 | 9 | 8 | 8 | 7 | 8 | 8 |
| | | | | | | | | | 1 | 5 | 4 | 8 | 6 | 6 | 6 | 7 | 5 | 7 | 8 | 8 | 7 | 7 | 7 | 8 | 8 |
| 58 | 9 | 8 | 9 | 8 | 8 | 9 | 8 | 8 | 5 | 8 | 7 | 8 | 8 | 7 | 9 | 9 | 8 | 9 | 9 | 8 | 8 | 8 | 8 | 8 | 8 |
| | | | | | | | | | 1 | 8 | 7 | 8 | 7 | 7 | 9 | 9 | 8 | 8 | 9 | 8 | 8 | 8 | 8 | 8 | 8 |
| 59 | 8 | 7 | 8 | 8 | 7 | 8 | 8 | 8 | 5 | 7 | 7 | 9 | 8 | 7 | 9 | 8 | 8 | 9 | 9 | 9 | 8 | 8 | 9 | 7 | 9 | 8 |
| | | | | | | | | | 1 | 7 | 7 | 8 | 7 | 7 | 8 | 7 | 8 | 9 | 9 | 9 | 8 | 8 | 7 | 8 | 6 |
| 60 | 7 | 7 | 8 | 7 | 7 | 8 | 8 | 7 | 5 | 7 | 6 | 7 | 6 | 7 | 8 | 8 | 7 | 8 | 9 | 9 | 7 | 8 | 8 | 8 | 8 |
| | | | | | | | | | 1 | 7 | 6 | 7 | 6 | 7 | 8 | 7 | 7 | 8 | 9 | 9 | 7 | 8 | 8 | 8 | 8 |
| 61 | 7 | 7 | 8 | 7 | 6 | 8 | 8 | 6 | 5 | 7 | 6 | 8 | 8 | 7 | 8 | 8 | 7 | 9 | 9 | 9 | 7 | 9 | 7 | 8 | 8 |
| | | | | | | | | | 1 | 6 | 6 | 6 | 6 | 7 | 8 | 7 | 7 | 8 | 9 | 8 | 7 | 7 | 7 | 7 | 8 |
| 62 | 6 | 6 | 8 | 7 | 6 | 8 | 8 | 8 | 5 | 7 | 6 | 7 | 7 | 7 | 7 | 7 | 7 | 7 | 9 | 9 | 8 | 7 | 7 | 7 | 8 |
| | | | | | | | | | 1 | 3 | 4 | 7 | 7 | 6 | 7 | 6 | 7 | 6 | 9 | 8 | 8 | 5 | 7 | 7 | 8 |
| 65 | 6 | 6 | 7 | 7 | | 5 | | | 5 | 5 | 5 | 8 | 7 | 3 | 6 | 3 | 3 | 5 | 8 | 6 | 5 | | 4 | 2 | |
| | | | | | | | | | 1 | 3 | | 5 | 3 | | 4 | | | 2 | 2 | 3 | 2 | | 3 | | |
| 66 | 7 | 6 | 7 | 7 | 3 | 7 | 7 | 2 | 5 | 5 | 5 | 7 | 6 | 6 | 7 | 8 | 8 | 8 | 9 | 8 | 7 | 7 | 7 | 8 | |
| | | | | | | | | | 1 | 2 | 4 | 7 | 6 | 2 | 7 | 6 | 5 | 5 | 8 | 8 | 6 | 3 | 6 | 6 | |
| 67 | 7 | 6 | 7 | 7 | 4 | 7 | 4 | | 5 | 7 | 6 | 7 | 6 | 7 | 8 | 5 | 6 | 8 | 9 | 8 | 7 | 3 | 6 | 3 | |
| | | | | | | | | | 1 | 5 | 6 | 7 | 6 | 5 | 7 | 4 | 4 | 5 | 9 | 7 | 5 | | 4 | 1 | |
| 68 | 7 | 7 | 7 | 7 | 8 | 8 | 8 | 8 | 5 | 7 | 6 | 8 | 7 | 7 | 9 | 8 | 7 | 9 | 9 | 9 | 8 | 9 | 7 | 8 | 8 |
| | | | | | | | | | 1 | 7 | 5 | 8 | 6 | 7 | 9 | 7 | 7 | 9 | 9 | 9 | 8 | 9 | 7 | 8 | 8 |
| 69 | 7 | 6 | 8 | 7 | 7 | 8 | 8 | 6 | 5 | 7 | 6 | 8 | 6 | 7 | 8 | 8 | 8 | 8 | 9 | 9 | 7 | 7 | 6 | 8 | 8 |
| | | | | | | | | | 1 | 7 | 4 | 6 | 6 | 7 | 8 | 8 | 5 | 5 | 9 | 9 | 7 | 7 | 6 | 8 | 8 |
| 70 | 7 | 6 | 8 | 7 | 7 | 8 | 9 | 6 | 5 | 6 | 6 | 8 | 6 | 7 | 8 | 7 | 8 | 9 | 9 | 9 | 7 | 9 | 7 | 8 | 8 |
| | | | | | | | | | 1 | 5 | 5 | 7 | 6 | 7 | 8 | 7 | 8 | 7 | 9 | 9 | 7 | 6 | 6 | 8 | 8 |
| 71 | | | | | | | 3 | | 5 | | | 2 | | | 3 | 4 | | | | | | | 2 | 5 | |
| | | | | | | | | | 1 | | | | | | | 1 | | | | | | | | 2 | |
| 72 | | | | | 4 | 3 | | | 5 | | | | | | 2 | 5 | | | | | | | | | |
| | | | | | | | | | 1 | | | | | | | 2 | | | | | | | | | |
| 73 | 5 | 5 | 2 | 7 | | 6 | 5 | | 5 | 2 | 6 | 6 | 7 | 2 | 7 | 6 | 5 | 2 | 3 | 2 | 4 | 2 | 3 | 3 | |
| | | | | | | | | | 1 | 1 | 3 | 3 | 6 | | 4 | 4 | 3 | 1 | | | 1 | | | 1 | |
| 74 | | | | | 3 | 5 | | | 5 | | | 2 | | 4 | 3 | 9 | 4 | | | | | | | 7 | |
| | | | | | | | | | 1 | | | | | | 1 | 8 | | | | | | | | 4 | |
| 75 | 5 | 7 | 7 | 7 | 2 | 5 | 4 | | 5 | 5 | 6 | 7 | 7 | 5 | 7 | 6 | 3 | 6 | 8 | 7 | 5 | 2 | 6 | 2 | |
| | | | | | | | | | 1 | 4 | 4 | 7 | 6 | 3 | 7 | 4 | 1 | 4 | 7 | 6 | 4 | | 4 | | |
| 76 | 7 | 6 | 5 | 7 | | 6 | 3 | 1 | 5 | 5 | 4 | 7 | 6 | 5 | 7 | 7 | 4 | 5 | 9 | 7 | 7 | 3 | 5 | 2 | |
| | | | | | | | | | 1 | 4 | 3 | 6 | 6 | 3 | 6 | 4 | 1 | 3 | 6 | 4 | 5 | | 4 | | |
| 77 | | | | | | | | | 5 | | | | 3 | 4 | 4 | | | 4 | 4 | 3 | 4 | | 5 | 7 | 7 |
| | | | | | | | | | 1 | | | | | 1 | 2 | | | 1 | | | | 2 | 5 | 7 |
| 78 | 8 | 7 | 8 | 8 | 7 | 8 | 8 | 7 | 5 | 8 | 7 | 8 | 8 | 8 | 8 | 8 | 8 | 9 | 9 | 9 | 9 | 9 | 7 | 8 | 8 |
| | | | | | | | | | 1 | 7 | 7 | 8 | 8 | 7 | 8 | 8 | 8 | 8 | 9 | 9 | 8 | 7 | 7 | 8 | 7 |
| 79 | 8 | 7 | 9 | 8 | 9 | 9 | 8 | 7 | 5 | 7 | 7 | 8 | 8 | 7 | 8 | 8 | 7 | 9 | 9 | 9 | 9 | 9 | 8 | 8 | 8 |
| | | | | | | | | | 1 | 6 | 7 | 7 | 8 | 7 | 8 | 7 | 7 | 9 | 9 | 9 | 9 | 8 | 8 | 8 | 8 |
| 80 | 7 | 7 | 8 | 7 | 7 | 8 | 7 | 7 | 5 | 5 | 6 | 7 | 7 | 7 | 8 | 8 | 6 | 8 | 9 | 8 | 8 | 8 | 7 | 7 | 7 |
| | | | | | | | | | 1 | 3 | 5 | 4 | 6 | 7 | 8 | 7 | 5 | 7 | 8 | 8 | 7 | 5 | 7 | 7 | 5 |
| 81 | 7 | 7 | 8 | 8 | 7 | 8 | 8 | 7 | 5 | 7 | 6 | 8 | 7 | 8 | 8 | 8 | 8 | 9 | 9 | 9 | 8 | 8 | 7 | 8 | 7 |
| | | | | | | | | | 1 | 7 | 6 | 7 | 7 | 8 | 8 | 8 | 7 | 8 | 9 | 9 | 8 | 8 | 7 | 8 | 7 |
| 82 | 7 | 7 | 8 | 7 | 7 | 8 | 6 | 7 | 5 | 8 | 6 | 8 | 7 | 7 | 8 | 7 | 7 | 9 | 9 | 9 | 7 | 8 | 7 | 8 | 8 |
| | | | | | | | | | 1 | 6 | 6 | 7 | 7 | 7 | 8 | .7 | | 6 | 9 | 9 | 7 | 6 | 7 | 7 | 7 |
| 83 | 7 | 7 | 8 | 7 | 6 | 7 | 7 | 6 | 5 | 8 | 6 | 8 | 8 | 7 | 8 | 8 | 8 | 8 | 9 | 9 | 7 | 6 | 6 | 8 | 8 |
| | | | | | | | | | 1 | 7 | 6 | 7 | 7 | 7 | 7 | 7 | 7 | 8 | 9 | 9 | 7 | 6 | 6 | 7 | 7 |
| 84 | | | | | 4 | | | | 5 | 2 | | | 2 | | 5 | 3 | 2 | | | | | | 2 | | |
| | | | | | | | | | 1 | | | | | 1 | | 3 | | | | | | | | | |

TABLE II-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 85 | 2 | 6 | 8 | 4 | 5 | 8 | 8 | 3 | 5 | | 4 | 7 | 3 | 3 | 8 | 7 | 7 | | | 8 | 4 | 6 | 7 | 8 | 2 |
| | | | | | | | | | 1 | | 1 | 6 | 1 | 1 | 6 | 7 | 6 | | | 6 | | 2 | 6 | 7 | |
| 86 | 5 | 7 | 7 | 7 | 3 | 7 | 6 | 3 | 5 | 6 | 7 | 7 | 7 | 4 | 7 | 7 | 6 | 7 | 8 | 8 | 6 | 6 | 6 | 8 | 2 |
| | | | | | | | | | 1 | 3 | 6 | 5 | 5 | | 5 | 6 | 3 | 3 | 5 | 6 | 4 | 2 | 6 | 5 | 1 |
| 87 | 7 | 7 | 2 | 5 | 4 | 2 | 2 | | 5 | 6 | 6 | 7 | 6 | 6 | 6 | 6 | 6 | 3 | 8 | 4 | | 3 | 2 | 2 | |
| | | | | | | | | | 1 | 2 | 2 | 5 | 4 | 4 | 4 | 4 | 3 | | 4 | | | | 1 | | |
| 88 | | | | | | | | | 5 | | | 2 | 3 | 4 | 6 | 5 | | | | | | | | | |
| | | | | | | | | | 1 | | | 1 | 2 | 3 | 6 | 3 | | | | | | | | | |
| 89 | 3 | 6 | 3 | 2 | 3 | 6 | 5 | 3 | 5 | 3 | 6 | 7 | 6 | 5 | 7 | 7 | 3 | 3 | 5 | 6 | 4 | 2 | 6 | 5 | |
| | | | | | | | | | 1 | 2 | 5 | 6 | 5 | 5 | 6 | 5 | 2 | 1 | 3 | 5 | 2 | | 3 | 2 | |
| 90 | 7 | 7 | 8 | 7 | 7 | 8 | 8 | 7 | 5 | 7 | 7 | 8 | 7 | 7 | 8 | 8 | 8 | 9 | 9 | 9 | 7 | 8 | 7 | 8 | 7 |
| | | | | | | | | | 1 | 7 | 6 | 7 | 7 | 7 | 7 | 8 | 8 | 8 | 8 | 9 | 7 | 6 | 7 | 8 | 7 |
| 91 | 7 | 7 | 8 | 7 | 7 | 8 | 8 | 7 | 5 | 7 | 7 | 8 | 8 | 7 | 8 | 8 | 8 | 9 | 9 | 9 | 8 | 9 | 7 | 8 | 7 |
| | | | | | | | | | 1 | 7 | 6 | 8 | 7 | 7 | 8 | 8 | 8 | 9 | 9 | 9 | 7 | 8 | 7 | 8 | 7 |
| 92 | 7 | 7 | 8 | 7 | 6 | 7 | 8 | 7 | 5 | 7 | 7 | 8 | 7 | 6 | 7 | 8 | 7 | 8 | * | 8 | 7 | 6 | 7 | 7 | 3 |
| | | | | | | | | | 1 | 7 | 7 | 8 | 7 | 6 | 7 | 7 | 8 | 6 | * | 8 | 6 | 4 | 7 | 7 | 3 |
| 93 | 7 | 7 | 8 | 7 | 6 | 8 | 8 | 7 | 5 | 7 | 6 | 8 | 6 | 7 | 8 | 8 | 8 | 8 | 9 | 9 | 7 | 8 | 7 | 8 | 7 |
| | | | | | | | | | 1 | 4 | 6 | 7 | 6 | 7 | 7 | 8 | 8 | 8 | 9 | 9 | 6 | 6 | 7 | 7 | 4 |
| 94 | 8 | 8 | 8 | 8 | 7 | 8 | 8 | 6 | 5 | 7 | 8 | 9 | 8 | 8 | 8 | 8 | 8 | 9 | 9 | 9 | 8 | 8 | 7 | 7 | 7 |
| | | | | | | | | | 1 | 7 | 8 | 8 | 7 | 7 | 8 | 8 | 8 | 8 | 9 | 9 | 8 | 8 | 7 | 7 | 7 |
| 95 | 8 | 8 | 8 | 9 | 7 | 8 | 9 | 7 | 5 | 7 | 8 | 8 | 8 | 7 | 8 | 9 | 9 | 9 | 9 | 9 | 7 | 7 | 8 | 7 | 4 |
| | | | | | | | | | 1 | 7 | 8 | 8 | 8 | 7 | 8 | 8 | 8 | 8 | 9 | 9 | 7 | 7 | 7 | 7 | 3 |
| 96 | 8 | 8 | 8 | 8 | 7 | 8 | 9 | 7 | 5 | 7 | 8 | 9 | 8 | 7 | 8 | 8 | 8 | 8 | 9 | 9 | 8 | 8 | 7 | 7 | 7 |
| | | | | | | | | | 1 | 7 | 7 | 8 | 7 | 7 | 7 | 7 | 8 | 8 | 9 | 9 | 7 | 7 | 7 | 7 | 7 |
| 97 | 8 | 8 | 8 | 7 | 6 | 7 | 8 | 7 | 5 | 8 | 8 | 8 | 8 | 7 | 8 | 9 | 8 | 7 | 8 | 8 | 8 | 7 | 7 | 7 | 5 |
| | | | | | | | | | 1 | 6 | 7 | 8 | 7 | 7 | 7 | 8 | 8 | 5 | 8 | 8 | 7 | 7 | 7 | 7 | 4 |
| 98 | 7 | 8 | 8 | 7 | 7 | 7 | 8 | 8 | 5 | 7 | 8 | 8 | 7 | 7 | 7 | 8 | 7 | 3 | 8 | 8 | 6 | 3 | 7 | 5 | 2 |
| | | | | | | | | | 1 | 7 | 8 | 8 | 7 | 7 | 7 | 8 | 7 | 2 | 7 | 8 | 6 | 2 | 6 | 5 | 2 |
| 99 | 7 | 7 | 7 | 6 | 5 | 7 | 7 | 7 | 5 | 7 | 8 | 7 | 7 | 7 | 7 | 7 | 7 | 4 | 8 | 8 | 7 | 5 | 6 | 5 | * |
| | | | | | | | | | 1 | 4 | 7 | 7 | 6 | 7 | 6 | 6 | 6 | 2 | 8 | 8 | 6 | 2 | 3 | 4 | |
| 100 | 6 | 7 | 7 | 6 | 4 | 7 | 8 | 8 | 5 | 7 | 8 | 8 | 7 | 7 | 8 | 7 | 8 | 4 | 8 | 8 | 7 | 2 | 4 | 7 | 2 |
| | | | | | | | | | 1 | 5 | 6 | 8 | 6 | 7 | 8 | 7 | 5 | 2 | 7 | 8 | 6 | 1 | 2 | 4 | |
| 101 | 7 | 7 | 8 | 6 | 7 | 7 | 8 | 8 | 5 | 7 | 7 | 8 | 7 | 7 | 8 | 9 | 8 | 8 | 9 | 9 | 7 | 7 | 7 | 7 | 7 |
| | | | | | | | | | 1 | 6 | 7 | 8 | 6 | 7 | 7 | 8 | 8 | 8 | 8 | 7 | 6 | 3 | 6 | 6 | 7 |
| 102 | 7 | 7 | 8 | 7 | 7 | 7 | 8 | 7 | 5 | 7 | 7 | 8 | 7 | 7 | 8 | 8 | 8 | 8 | 9 | 9 | 7 | 8 | 7 | 7 | 7 |
| | | | | | | | | | 1 | 7 | 7 | 7 | 6 | 7 | 7 | 8 | 8 | 7 | 9 | 8 | 7 | 5 | 6 | 6 | 7 |
| 103 | 7 | 7 | 7 | 6 | 6 | 7 | 8 | 7 | 5 | 7 | 7 | 8 | 7 | 6 | 8 | 8 | 8 | 8 | 9 | 9 | 7 | 7 | 7 | 8 | 7 |
| | | | | | | | | | 1 | 7 | 7 | 7 | 6 | 6 | 6 | 8 | 7 | 8 | 9 | 9 | 7 | 7 | 7 | 7 | 7 |
| 104 | 7 | 7 | 8 | 7 | 6 | 7 | 8 | 8 | 5 | 7 | 7 | 8 | 7 | 6 | 8 | 8 | 8 | 8 | 9 | 9 | 7 | 6 | 7 | 8 | 8 |
| | | | | | | | | | 1 | | 3 | 7 | 6 | 6 | 7 | 8 | 8 | 8 | 9 | 9 | 7 | 4 | 7 | 8 | 7 |
| 105 | 5 | 7 | 7 | 6 | 4 | 6 | 6 | 6 | 5 | 7 | 7 | 8 | 7 | 6 | 7 | 8 | 7 | 4 | 7 | 7 | 4 | 4 | 5 | 4 | |
| | | | | | | | | | 1 | 7 | 7 | 8 | 7 | 6 | 7 | 7 | 7 | 3 | 7 | 7 | 3 | 3 | 4 | 3 | |
| 106 | 6 | 7 | 8 | 7 | 6 | 7 | 7 | 7 | 5 | 8 | 7 | 8 | 7 | 6 | 7 | 8 | 7 | 8 | 8 | 8 | 7 | 4 | 7 | 6 | 4 |
| | | | | | | | | | 1 | 7 | 7 | 8 | 7 | 6 | 7 | 8 | 7 | 7 | 8 | 7 | 4 | 3 | 5 | 6 | 2 |
| 107 | 7 | 8 | 8 | 8 | 6 | 7 | 7 | 7 | 5 | 7 | 7 | 8 | 7 | 6 | 7 | 8 | 7 | 8 | 9 | 9 | 7 | 6 | 7 | 7 | 5 |
| | | | | | | | | | 1 | | | 5 | 3 | 2 | 3 | 3 | 2 | 4 | 7 | 8 | 7 | 4 | 7 | 5 | |
| 108 | 7 | 7 | 8 | 7 | 7 | 7 | 7 | 7 | 5 | 7 | 7 | 8 | 6 | 6 | 8 | 8 | 6 | 8 | 9 | 9 | 8 | 8 | 7 | 8 | 7 |
| | | | | | | | | | 1 | 5 | 6 | 7 | 6 | 6 | 7 | 7 | 6 | 8 | 9 | 8 | 7 | 6 | 7 | 8 | 6 |
| 109 | 7 | 7 | 8 | 7 | 6 | 7 | 7 | 6 | 5 | 8 | 7 | 8 | 7 | 6 | 7 | 8 | 7 | 8 | 9 | 9 | 7 | 5 | 7 | 7 | 3 |
| | | | | | | | | | 1 | 7 | 7 | 8 | 6 | 6 | 7 | 7 | 7 | 7 | 8 | 8 | 5 | 3 | 7 | 7 | 3 |
| 111 | | 5 | 5 | 3 | | 4 | 3 | 2 | 5 | 4 | 6 | 7 | 7 | 7 | 6 | 5 | 6 | | 5 | 4 | 4 | | 3 | 3 | |
| | | | | | | | | | 1 | | 2 | 5 | 4 | 4 | 6 | 4 | 2 | | | 1 | 1 | | | 1 | |
| 112 | 7 | 8 | 8 | 6 | 6 | 7 | 8 | 8 | 5 | 7 | 7 | 7 | 7 | 7 | 8 | 8 | 7 | 6 | 8 | 9 | 6 | 5 | 6 | 6 | 3 |
| | | | | | | | | | 1 | 6 | 7 | 7 | 7 | 7 | 7 | 8 | 7 | 4 | 8 | 9 | 6 | 4 | 5 | 6 | |
| 113 | 7 | 8 | 8 | 7 | 7 | 8 | 8 | 7 | 5 | 7 | 7 | 8 | 7 | 7 | 8 | 9 | 7 | 9 | 8 | 8 | 7 | 3 | 6 | 6 | |
| | | | | | | | | | 1 | 7 | 7 | 8 | 7 | 6 | 8 | 8 | 7 | 7 | 5 | 8 | 5 | 1 | 6 | 5 | |
| 114 | 6 | 7 | 7 | 7 | 6 | 7 | 8 | 7 | 5 | 6 | 6 | 7 | 6 | 6 | 7 | 7 | 7 | 6 | 6 | 6 | 5 | 2 | 5 | 4 | 4 |
| | | | | | | | | | 1 | 5 | 5 | 7 | 6 | 6 | 6 | 7 | 5 | 4 | 5 | 4 | 2 | | 3 | 1 | |
| 115 | 7 | 7 | 8 | 7 | 6 | 8 | 8 | 8 | 5 | 7 | 6 | 7 | 7 | 6 | 8 | 8 | 7 | 7 | 8 | 8 | 7 | 8 | 6 | 8 | 7 |
| | | | | | | | | | 1 | | 5 | 6 | 7 | 6 | 8 | 8 | 7 | 6 | 8 | 6 | 7 | 6 | 6 | 5 | |
| 116 | 4 | 4 | 6 | 6 | 5 | 6 | 7 | 6 | 5 | 4 | | 7 | 6 | 6 | 8 | 8 | 5 | 5 | 5 | 8 | 5 | 5 | 6 | 5 | 4 |
| | | | | | | | | | 1 | 3 | | 7 | 6 | 6 | 8 | 8 | 4 | 5 | 5 | 8 | 4 | 4 | 6 | 5 | 4 |
| 117 | 7 | 7 | 9 | 8 | 6 | 8 | 8 | 8 | 5 | 7 | 7 | 8 | 6 | 6 | 8 | 9 | 8 | 9 | 9 | 9 | 7 | 8 | 7 | 8 | 6 |
| | | | | | | | | | 1 | 7 | 7 | 7 | 6 | 6 | 8 | 8 | 8 | 9 | 9 | 8 | 6 | 7 | 6 | 8 | 5 |
| 118 | 7 | 7 | 8 | 7 | 4 | 8 | 7 | 6 | 5 | 4 | 7 | 8 | 6 | 2 | 9 | 8 | 6 | 7 | 9 | 9 | 7 | 7 | 7 | 8 | 2 |
| | | | | | | | | | 1 | | 6 | 7 | 6 | | 8 | 7 | 3 | 4 | 9 | 8 | 7 | 2 | 7 | 7 | |
| 119 | 7 | 7 | 8 | 8 | 6 | 9 | 8 | 6 | 5 | 4 | 7 | 9 | 7 | 5 | 9 | 7 | 6 | 6 | 9 | 9 | 8 | 7 | 7 | 8 | 2 |
| | | | | | | | | | 1 | | 6 | 8 | 6 | 3 | 8 | 6 | 3 | 1 | 9 | 9 | 7 | 4 | 7 | 7 | |
| 120 | 8 | 7 | 9 | 8 | 8 | 8 | 8 | 7 | 5 | 7 | 7 | 9 | 7 | 7 | 9 | 8 | 7 | 9 | 9 | 9 | 8 | 9 | 7 | 8 | 8 |
| | | | | | | | | | 1 | 7 | 7 | 9 | 7 | 6 | 8 | 8 | 6 | 7 | 9 | 9 | 7 | 8 | 7 | 7 | 7 |
| 121 | | | | | 7 | 4 | | | 5 | | | 2 | 3 | 2 | 9 | 4 | 4 | 4 | 5 | 4 | 5 | | 7 | 3 | |
| | | | | | | | | | 1 | | | | | 2 | 7 | 2 | 2 | 1 | 2 | 2 | 3 | | 7 | | |
| 122 | 2 | 4 | 2 | 3 | | 2 | 6 | 3 | 5 | 4 | 5 | 8 | 6 | 6 | 8 | 9 | 8 | 3 | 8 | 5 | 2 | 4 | 5 | 5 | 2 |
| | | | | | | | | | 1 | 2 | 2 | 7 | 4 | 3 | 8 | 7 | .6 | | 6 | 2 | 1 | 2 | 1 | | 1 |
| 123 | | | | | 3 | 2 | | | 5 | 4 | 4 | 7 | 4 | 2 | 6 | 5 | 7 | | | | | | | | |
| | | | | | | | | | 1 | | | 3 | | 1 | 4 | 3 | 4 | | | | | | | | |
| 124 | | 2 | 3 | | | 8 | 3 | | 5 | 3 | 2 | 3 | | | 8 | 4 | 1 | | | 2 | | | 6 | | |
| | | | | | | | | | 1 | 1 | | 1 | | | 7 | 2 | | | | | | | 2 | | |

TABLE II-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 125 | 7 | 8 | 8 | 7 | 2 | 8 | 6 | 2 | 5 | 7 | 7 | 8 | 6 | 4 | 8 | 8 | 7 | 4 | 9 | 9 | 6 | 4 | 7 | 7 | 3 |
| | | | | | | | | | 1 | 4 | 6 | 7 | 4 | 1 | 8 | 7 | 4 | 3 | 8 | 8 | 6 | | 7 | 7 | |
| 126 | 7 | 8 | 8 | 7 | 2 | 8 | 5 | 2 | 5 | 7 | 7 | 8 | 6 | 6 | 9 | 8 | 6 | 4 | 8 | 9 | 7 | 2 | 7 | 6 | 3 |
| | | | | | | | | | 1 | 4 | 6 | 8 | 5 | 2 | 8 | 5 | 2 | | 7 | 8 | 6 | | 7 | 2 | 2 |
| 127 | 7 | 7 | 7 | 7 | 8 | 7 | 8 | 4 | 5 | 7 | 6 | 7 | 6 | 7 | 6 | 5 | 6 | 7 | 9 | 8 | 7 | 7 | 7 | 8 | |
| | | | | | | | | | 1 | 4 | 4 | 6 | 4 | 6 | 2 | 2 | | 4 | 8 | 7 | 5 | 4 | 6 | | |
| 128 | | 6 | 6 | 5 | 5 | 7 | 5 | | 5 | | 2 | 2 | 5 | 6 | 3 | 4 | | 4 | 6 | 6 | 6 | 6 | 7 | 6 | |
| | | | | | | | | | 1 | | | | 2 | | 1 | 3 | | 2 | 2 | 4 | 2 | | 4 | 2 | |
| 129 | | 5 | 5 | 5 | 2 | 7 | 5 | | 5 | 1 | | 2 | 2 | 6 | 6 | 5 | 4 | 7 | 7 | 6 | 6 | 4 | 7 | 4 | |
| | | | | | | | | | 1 | | | | | 4 | 2 | 2 | | | 2 | 1 | 1 | | 3 | 1 | |
| 130 | | 5 | 5 | 4 | 4 | 6 | 3 | | 5 | | | 2 | 4 | 4 | 6 | 4 | 4 | 2 | 6 | 6 | 5 | 2 | 6 | 3 | |
| | | | | | | | | | 1 | | | | | | 3 | 1 | 1 | | 2 | 1 | 1 | | 2 | | |
| 131 | 7 | 7 | 8 | 7 | 7 | 7 | 4 | 2 | 5 | 4 | 5 | 8 | 7 | 7 | 8 | 5 | 4 | 4 | 9 | 8 | 7 | 7 | 7 | 4 | |
| | | | | | | | | | 1 | 1 | 2 | 5 | 3 | 6 | 5 | 3 | | | 8 | 6 | 6 | 2 | 6 | | |
| 132 | | | | 2 | 5 | 7 | 3 | | 5 | 2 | 3 | 5 | 6 | 7 | 8 | 7 | 6 | 2 | 4 | 5 | 5 | 3 | 7 | 4 | |
| | | | | | | | | | 1 | | 1 | 2 | 3 | 5 | 7 | 2 | 2 | | | 1 | 1 | | 4 | 1 | |
| 133 | | | | | 2 | 7 | 2 | | 5 | 2 | 2 | 5 | 7 | 7 | 8 | 7 | 5 | | | 5 | 4 | 4 | 7 | 4 | |
| | | | | | | | | | 1 | | | 3 | 5 | 4 | 6 | 4 | 3 | | | | | | 3 | 1 | |
| 134 | | | | | | | | | 5 | 2 | | | 3 | 3 | 5 | 3 | 2 | | | | | | | | |
| | | | | | | | | | 1 | | | | | | 3 | 1 | 1 | | | | | | | | |
| 135 | | | | | | 4 | 2 | | 5 | | | 2 | | | 7 | 7 | 4 | | | | | | | | |
| | | | | | | | | | 1 | | | 1 | | | 4 | 2 | 1 | | | | | | | | |
| 136 | | | | | | | | | 5 | 2 | | | 4 | | 7 | 5 | | | | | | | | | |
| | | | | | | | | | 1 | | | | | | 3 | 2 | | | | | | | | | |
| 137 | | 3 | | | 2 | 6 | 5 | | 5 | 2 | 4 | 5 | 6 | 7 | 8 | 7 | 5 | 2 | 7 | 6 | 4 | 3 | 7 | 5 | |
| | | | | | | | | | 1 | | 1 | 2 | 3 | 6 | 7 | 4 | 2 | | 5 | 2 | | | 5 | 2 | |
| 138 | 3 | 4 | 4 | 3 | 2 | 4 | 2 | | 5 | 3 | 4 | 8 | 6 | 6 | 8 | 8 | 6 | 3 | 5 | 8 | 4 | 2 | 5 | 5 | |
| | | | | | | | | | 1 | | | 6 | 5 | 3 | 6 | 5 | 3 | 2 | 3 | 7 | 1 | | 2 | 2 | |
| 139 | * | * | * | * | * | * | * | * | 5 | | | 2 | 3 | | 7 | 4 | 4 | | | | | | 2 | 2 | |
| | | | | | | | | | 1 | | | | 1 | | 3 | | | | | | | | | | |
| 140 | 6 | 7 | 8 | 7 | | 7 | 7 | 2 | 5 | 4 | 6 | 7 | 6 | 4 | 9 | 8 | 5 | 3 | 8 | 8 | 6 | 4 | 6 | 8 | 5 |
| | | | | | | | | | 1 | 1 | 4 | 6 | 5 | 3 | 7 | 7 | 4 | 1 | 6 | 8 | 4 | 1 | 6 | 6 | 4 |
| 141 | 6 | 7 | 7 | 7 | 1 | 8 | 8 | 2 | 5 | 4 | 6 | 8 | 7 | 4 | 8 | 7 | 6 | 4 | 7 | 8 | 6 | 4 | 7 | 7 | 5 |
| | | | | | | | | | 1 | 1 | 4 | 7 | 6 | 1 | 7 | 6 | 4 | 3 | 6 | 7 | 5 | | 7 | 7 | |
| 142 | 4 | 7 | 7 | 5 | 2 | 8 | 7 | 3 | 5 | 4 | 4 | 6 | 3 | 2 | 8 | 8 | 3 | 2 | 7 | 7 | 4 | 2 | 7 | 6 | 2 |
| | | | | | | | | | 1 | 1 | 2 | 4 | 2 | | 8 | 5 | 2 | 2 | 5 | 6 | 3 | | 7 | 4 | 1 |
| 143 | 6 | 7 | 7 | 5 | 3 | 8 | 7 | 4 | 5 | 4 | 6 | 6 | 6 | 5 | 8 | 8 | 6 | 2 | 7 | 7 | 6 | 2 | 7 | 7 | |
| | | | | | | | | | 1 | 1 | 5 | 5 | 3 | 2 | 6 | 5 | 3 | 2 | 6 | 6 | 3 | | 6 | 5 | |
| 144 | 7 | 7 | 8 | 7 | 7 | 7 | 8 | 6 | 5 | 5 | 7 | 8 | 7 | 6 | 8 | 8 | 6 | 7 | 9 | 9 | 7 | 6 | 7 | 7 | 3 |
| | | | | | | | | | 1 | 5 | 6 | 7 | 6 | 7 | 7 | 7 | 5 | 6 | 8 | 8 | 7 | 4 | 7 | 6 | 2 |
| 145 | 5 | 6 | 7 | 6 | 4 | 7 | 7 | 4 | 5 | | 4 | 6 | 4 | 4 | 6 | 5 | 2 | 4 | 7 | 5 | 4 | 2 | 5 | 1 | 6 |
| | | | | | | | | | 1 | | 1 | 4 | 3 | 1 | 5 | 3 | 1 | 1 | 1 | 2 | 1 | | 4 | | |
| 146 | | | | | | 3 | | | 5 | 2 | | 6 | 3 | 5 | 6 | 3 | 5 | | | | | | | | |
| | | | | | | | | | 1 | 1 | | 4 | 3 | 2 | 3 | 1 | | | | | | | | | |
| 147 | 3 | 6 | 6 | 3 | 7 | 7 | 5 | 2 | 5 | 4 | 3 | 6 | 4 | 7 | 7 | 8 | 5 | 6 | 8 | 8 | 5 | 7 | 6 | 7 | |
| | | | | | | | | | 1 | 1 | 1 | 2 | 2 | 6 | 5 | 5 | 1 | | 2 | 3 | 2 | 2 | 3 | 4 | |
| 148 | 6 | 7 | 6 | 7 | 6 | 3 | 5 | 2 | 5 | 7 | 7 | 7 | 7 | 7 | 7 | 6 | 6 | 7 | 9 | 8 | 7 | 7 | 7 | 7 | |
| | | | | | | | | | 1 | 4 | 6 | 6 | 6 | 5 | 5 | 5 | 4 | 4 | 8 | 6 | 5 | 2 | 3 | 2 | |
| 149 | 3 | 6 | 7 | 7 | 5 | 3 | 4 | 3 | 5 | 4 | 7 | 7 | 7 | 7 | 7 | 6 | 4 | 6 | 9 | 8 | 7 | 7 | 7 | 7 | 4 |
| | | | | | | | | | 1 | 2 | 6 | 6 | 6 | 2 | 5 | 3 | 1 | | 7 | 7 | 4 | | 3 | | |
| 150 | 4 | 6 | 6 | 6 | 4 | 3 | 5 | 2 | 5 | 4 | 5 | 7 | 7 | 5 | 7 | 5 | 5 | 6 | 8 | 8 | 6 | 3 | 5 | 2 | |
| | | | | | | | | | 1 | 2 | 2 | 4 | 3 | 2 | 6 | | 1 | | 4 | 4 | 3 | | 2 | 1 | |
| 151 | 8 | 8 | 8 | 7 | 6 | 8 | 7 | 2 | 5 | 7 | 7 | 8 | 7 | 6 | 9 | 7 | 7 | 8 | 8 | 8 | 7 | 4 | 6 | 8 | |
| | | | | | | | | | 1 | 4 | 6 | 6 | 7 | 4 | 6 | 5 | 5 | 6 | 7 | 7 | 6 | | 6 | 5 | |
| 152 | 7 | 7 | 8 | 7 | 5 | 8 | 6 | 5 | 5 | 7 | 7 | 8 | 7 | 7 | 8 | 6 | 7 | 9 | 9 | 8 | 7 | 7 | 7 | 7 | 5 |
| | | | | | | | | | 1 | 6 | 6 | 7 | 6 | 6 | 7 | 5 | 5 | 8 | 9 | 8 | 6 | 2 | 6 | 4 | |
| 153 | 8 | 8 | 8 | 7 | 6 | 8 | 8 | 7 | 5 | 7 | 6 | 7 | 7 | 7 | 8 | 8 | 7 | 8 | 8 | 8 | 7 | 7 | 7 | 6 | 8 |
| | | | | | | | | | 1 | | 3 | 4 | 7 | 6 | 7 | 6 | 6 | 5 | 6 | 8 | 6 | 4 | 7 | 6 | 2 |
| 154 | 4 | 3 | 2 | 5 | | 4 | 2 | | 5 | 4 | 6 | 7 | 7 | 6 | 7 | 2 | 4 | 4 | | 4 | 5 | | 5 | 2 | |
| | | | | | | | | | 1 | 2 | 2 | 4 | 6 | 2 | 7 | | 3 | | | 2 | | | 3 | | |
| 155 | 6 | 6 | 7 | 6 | 2 | 6 | 4 | 5 | 5 | 6 | 4 | 8 | 7 | 7 | 7 | 7 | 5 | 7 | 8 | 8 | 6 | 4 | 6 | 3 | 2 |
| | | | | | | | | | 1 | 6 | 4 | 7 | 7 | 6 | 5 | 5 | 4 | 6 | 7 | 8 | 4 | 2 | 2 | 1 | |
| 156 | 7 | 8 | 7 | 7 | 3 | | 7 | 3 | 5 | 5 | 8 | 7 | 7 | 6 | 8 | 8 | 5 | 4 | 8 | 7 | 5 | 2 | 5 | 2 | |
| | | | | | | | | | 1 | 3 | 7 | 7 | 5 | 7 | 7 | 3 | 2 | | 6 | 7 | 4 | | 3 | 2 | |
| 157 | 7 | 6 | 7 | 6 | 2 | 7 | 6 | 4 | 5 | 7 | 3 | 7 | 7 | 5 | 8 | 8 | 7 | 7 | 8 | 9 | 7 | 2 | 7 | 5 | 3 |
| | | | | | | | | | 1 | 4 | 3 | 7 | 7 | 2 | 7 | 6 | 5 | 6 | 8 | 8 | 6 | | 5 | 3 | 2 |
| 158 | 6 | 7 | 6 | 5 | 4 | 6 | 8 | 4 | 5 | 6 | 6 | 8 | 6 | 7 | 7 | 8 | 5 | 5 | 7 | 7 | 3 | 2 | 3 | 4 | 2 |
| | | | | | | | | | 1 | 4 | 5 | 6 | 6 | 7 | 6 | 8 | 4 | 2 | 5 | 5 | 2 | | 2 | 3 | |
| 159 | 7 | 7 | 7 | 7 | 3 | 7 | 4 | 6 | 5 | 7 | 7 | 7 | 7 | 7 | 8 | 7 | 6 | 8 | 8 | 9 | 7 | 4 | 7 | 5 | 3 |
| | | | | | | | | | 1 | 4 | 7 | 7 | 6 | 6 | 7 | 5 | 4 | 6 | 8 | 8 | 6 | 1 | 5 | 2 | |
| 160 | 7 | 7 | 7 | 7 | 4 | 7 | 4 | 3 | 5 | 6 | 7 | 7 | 6 | 6 | 8 | 8 | 5 | 7 | 8 | 8 | 6 | 4 | 7 | 7 | 2 |
| | | | | | | | | | 1 | 3 | 6 | 6 | 5 | 4 | 7 | 5 | 2 | 4 | 8 | 6 | 5 | 1 | 5 | 3 | |
| 161 | 6 | 7 | 8 | 7 | | 8 | 6 | 2 | 5 | 6 | 7 | 8 | 7 | 5 | 8 | 6 | 7 | 5 | 8 | 9 | 6 | 3 | 7 | 6 | |
| | | | | | | | | | 1 | 2 | 5 | 7 | 6 | 2 | 8 | 5 | 4 | 5 | 7 | 7 | 5 | | 6 | 1 | |
| 162 | 7 | 8 | 9 | 7 | 6 | 8 | 9 | 8 | 5 | 7 | 7 | 9 | 7 | 6 | 8 | 8 | 8 | 8 | 9 | 9 | 7 | 8 | 6 | 7 | 7 |
| | | | | | | | | | 1 | 5 | 7 | 8 | 6 | 6 | 8 | 8 | 6 | 8 | 9 | 9 | 7 | 7 | 6 | 7 | 6 |
| 163 | 3 | 8 | 7 | 7 | | | 3 | 4 | 5 | 6 | 7 | 8 | 7 | 7 | 7 | 7 | 5 | | 6 | 8 | 7 | 3 | | | 7 |
| | | | | | | | | | 1 | 4 | 5 | 8 | 6 | 5 | 6 | 4 | 2 | | | 6 | 3 | | | | |

TABLE II-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 164 | | 2 | 6 | 2 | 6 | 5 | 8 | | 5 | 3 | 3 | 6 | 5 | 5 | 7 | 7 | 7 | 2 | 4 | 4 | 2 | 2 | 8 | 8 | 2 |
| | | | | | | | | | 1 | 1 | | 2 | 2 | | 3 | 5 | 2 | | | | 2 | | 5 | 5 | |
| 166 | | | | | | | | | 5 | | | | | 4 | | | | | | | | | | | |
| | | | | | | | | | 1 | | | | | 1 | | | | | | | | | | | |
| 167 | 5 | 4 | 7 | 3 | 6 | 8 | 8 | 2 | 5 | 6 | 4 | 7 | 6 | 7 | 8 | 8 | 5 | 5 | 7 | 7 | 6 | 6 | 6 | 8 | 5 |
| | | | | | | | | | 1 | 2 | | 5 | 5 | 3 | 5 | 7 | 3 | 2 | | | 3 | | 3 | 4 | |
| 168 | | | | | | | | | 5 | 2 | 2 | 3 | 3 | 2 | 2 | | 2 | | | 2 | 2 | | 3 | | |
| | | | | | | | | | 1 | | | | 2 | | | | | | | | | | | | |

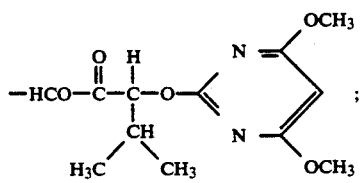

We claim:

1. A compound of the formula I

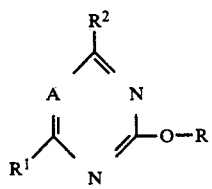

in which

A represents group CH;

$R^1$ and $R^2$ each independently represents a halogen atom, $C_{1-4}$ alkyl, $C_{1-4}$ alkoxy, $C_{1-4}$ alkylthio or mono- or di-$C_{1-4}$ alkylamino;

and R represents a group of the formula

(A)

in which $R^3$ represents a $C_{1-6}$ alkyl group optionally substituted by $C_{1-4}$ alkylthio; cyclohexyl; benzyl; phenyl optionally substituted by one or more substituents independently selected from halogen, trifluoromethyl, $C_{1-4}$ alkyl and ($C_{1-4}$ alkoxy) carbonyl; thienyl; carboxy; ($C_{1-4}$ alkoxy)carbonyl; ($C_{1-4}$ alkoxy)carbonylcarbonyl or de($C_{1-4}$ alkyl)carbamoyl; and $R^4$ represents a group $COR^6$ wherein $R^6$ represents hydroxy; $C_{1-4}$ alkoxy optionally substituted by halogen or $C_{1-4}$ alkoxy, $C_{1-4}$ alkylthio, phenyl, optionally substituted on the phenyl ring by one or more substituents independently selected from halogen and $C_{1-4}$ alkoxy, furyl, tetrahydrofuryl or thienyl; $C_{1-4}$ alkylthio; $C_{2-4}$ alkynyloxy; phenoxy optionally substituted by one or more substituents independently selected from $C_{1-4}$ alkyl, nitro, hydroxy ($C_{1-4}$) alkyl, and a group of the formula

phenylthio; amino optionally substituted by amino, di($C_{1-4}$) alkylamino or phenyl optionally substituted by carboxy or ($C_{1-4}$ alkoxy)carbonyl; or di($C_{1-4}$) alkylaminoxy;

or R represents a group of the formula $$\begin{array}{c} CR^9R^{10} \\ \| \\ -C-R^4 \end{array}$$ (B)

in which $R^4$ is as defined above and wherein one of $R^9$ and $R^{10}$ represents hydrogen and the other represents $C_{1-4}$ alkyl, or a carboxylic acid salt of a compound of formula I with an equivalent amount of an inorganic or organic cation.

2. A compound as claimed in claim 1, in which $R^1$ and $R^2$ each independently represent chlorine, methyl, methoxy, methylthio, methylamino or dimethylamino.

3. A compound as claimed in claim 1, in which $R^3$ represents $C_{2-6}$ alkyl, benzyl or an unsubstituted phenyl.

4. A compound as claimed in claim 3, in which $R^3$ represents isopropyl, n-propyl, i-butyl, n-butyl, s-butyl, t-butyl, benzyl or phenyl.

5. A compound as claimed in claim 1, in which $R^4$ represents $COR^6$ wherein $R^6$ represents hydroxy, $C_{1-4}$ alkoxy or optionally substituted amino.

6. A compound as claimed in claim 5, in which $R^4$ represents the group $COR^6$ in which $R^6$ represents hydroxy or $C_{1-4}$ alkoxy.

7. A carboxylic acid salt as claimed in claim 1, which is an alkali metal salt.

8. A compound as claimed in claim 1, wherein $R^1$ and $R^2$ are the same and each represents methyl or methoxy, and R represents a group of the formula (A) in which $R^3$ represents n-butyl, i-butyl, t-butyl or phenyl and $R^4$ represents carboxy or methoxycarbonyl.

9. A compound as claimed in claim 8, wherein $R^1$ is $CH_3$, $R^2$ is $CH_3$, $R^3$ is i-$C_4H_9$ and $R^4$ is COOH, or $R^1$ is $OCH_3$, $R^2$ is $OCH_3$, $R^3$ is i-$C_4H_9$ and $R^4$ is $CO_2CH_3$, or $R^1$ is $CH_3$, $R^2$ is $CH_3$, $R^3$ is phenyl and $R^4$ is $CO_2CH_3$.

10. A herbicidal composition which comprises an effective amount of the compound as claimed in claim 1 in association with a carrier.

11. A method of combating undesired plant growth at a locus which comprises treating the locus with an effective amount of a compound as claimed in claim 1.

12. A method of combating undesired plant growth at a locus which comprises treating the locus with an effective amount of a composition as claimed in claim 10.

* * * * *

UNITED STATES PATENT AND TRADEMARK OFFICE
CERTIFICATE OF CORRECTION

PATENT NO. : 5,139,563
DATED : August 18, 1992
INVENTOR(S) : Astles et al

It is certified that error appears in the above-indentified patent and that said Letters Patent is hereby corrected as shown below:

Column 33, line 62, (claim 1) "de($C_{1-4}$alkyl)carbamoyl" should read --di($C_{1-4}$alkyl)carbamoyl--.

Column 34, line 44-45, (claim 4) "n-propyl, i-butyl, n-butyl, s-butyl, t-butyl," should read --$\underline{n}$-propyl, $\underline{i}$-butyl, $\underline{n}$-butyl, $\underline{s}$-butyl, $\underline{t}$-butyl,--.

Column 34, line 57, (claim 8) "n-butyl, i-butyl, t-butyl" should read --$\underline{n}$-butyl, $\underline{i}$-butyl, $\underline{t}$-butyl--.

Column 34, lines 60 and 61, (claim 9) "i-$C_4H_9$" should read --$\underline{i}$-$C_4H_9$--.

Signed and Sealed this

Twenty-eighth Day of September, 1993

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,139,563

DATED : August 18, 1992

INVENTOR(S) : DAVID P. ASTLES ET AL.

It is certified that error appears in the above-identified patent and that said Letters Patent is hereby corrected as shown below:

On the title page of the patent, under "Inventors", --William John Hopwood, Tunstall, England-- should be added.

Signed and Sealed this

Seventeenth Day of May, 1994

Attest:

BRUCE LEHMAN

*Attesting Officer*   Commissioner of Patents and Trademarks